US009133451B2

(12) United States Patent
Cheng et al.

(10) Patent No.: US 9,133,451 B2
(45) Date of Patent: Sep. 15, 2015

(54) METHOD FOR MODULATING A BACTERIAL INVASION SWITCH

(71) Applicant: Research Foundation of the City University of New York, New York, NY (US)

(72) Inventors: Haiping Cheng, New York, NY (US); Shari Walcott, New York, NY (US); Haiyang Lu, New York, NY (US); Li Luo, New York, NY (US); Meghua Yang, New York, NY (US); Zahra Salehi, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 13/903,289

(22) Filed: May 28, 2013

(65) Prior Publication Data

US 2014/0010842 A1 Jan. 9, 2014

Related U.S. Application Data

(60) Provisional application No. 61/652,120, filed on May 25, 2012.

(51) Int. Cl.

| | |
|---|---|
| ***A61K 39/02*** | (2006.01) |
| ***C12N 9/99*** | (2006.01) |
| ***A01N 63/00*** | (2006.01) |
| ***C12N 1/36*** | (2006.01) |
| ***C12N 9/52*** | (2006.01) |

(52) U.S. Cl.

CPC *C12N 9/99* (2013.01); *A01N 63/00* (2013.01); *C12N 1/36* (2013.01); *C12N 9/52* (2013.01)

(58) Field of Classification Search

None

See application file for complete search history.

(56) References Cited

PUBLICATIONS

Singh, S.M. and : Cheng, H.; Lu, H. Corporate Source: Biology, Lehman College, Bronx, NY, United States. Source: Molecular Biology of the Cell, (Dec. 15, 2010) vol. 21, No. 24. Abstract Number: 403/B604. Meeting Info: Annual Meet of the American Society for Cell Biology, ASCB2010.* b ) Hai-Yang Lu, Li Luo, Meng-Hua Yang and Hai-Ping Cheng J. Bacteriol. 2012, 194(15):4029. DOI: 10.1128/JB.00313-12.*

Wu, Chih-Feng et al., "Acid-Induced Type VI Secretion System is Regulated by ExoR-ChvG/Chvl Signaling Cascade in Agrobacterium tumefaciens", also available at www.plospathogens.org, PLOS Pathogens, Sep. 2012, vol. 8, Issue 9, e1002938, pp. 1-18.

Lu, Hai-Yang et al., "Autoregulation of Sinorhizobium meliloti exoR gene expression", Microbiology (2010), 156, DOI 10.1099/mic.0.038547-0, pp. 2092-2101.

Li, Luoping, et al,, "A global pH sensor: Agrobacterium sensor protein ChvG regulates acid-inducible genes on its two chromosomes and Ti plasmid", PNAS, Sep. 17, 2002, vol. 99, No. 19, pp. 12369-12374.

Yao, Shi-Yi et al. "Sinorhizobium meliloti ExoR and ExoS Proteins Regulate both Succinoglycan and Flagellum Production", Journal of Bacteriology, Sep. 2004, vol. 186, No. 18, DOI: 10.1128/JB.186.18.6024-6049.2004, pp. 6042-6049.

Keating, David H. "The Sinorhizobium meliloti ExoR protein is required for the downregulation of IpsS transcription and succinoglycan biosynthesis in response to the divalent cations", Department of Microbiology and Immunology, Loyola University, Chicago, Maywood, IL, FEMS Microbiol Lett. 267 (2007) pp. 23-29.

Wells, Derek H. et al., "ExoR is genetically coupled to the ExoS-Chvl two-component system and located in the periplasm of Sinorhizobium meliloti", DOI: 10.1111/j.1365-2958.2007.05680.x, Molecular Microbiology (2007) 64(3), pp. 647-664.

!Chen, Esther J. et al., "The periplasmic regulator ExoR inhibits ExoS/Chvl two-component signalling in Sinorhizobium meliloti", Molecular Microbiology (2008) DOI: 10.1111/j.1365-2958.2008.06362.x, (14 pgs.).

Tomlinson, Amelia D. et al., "Agrobacterium tumefaciens ExoR represeses succinoglycan biosynthesis and is required for biofilm formation and motility", Cell and Molecular Biology of Microbes, Microbiology (2010), 156, 000-000, DOI: 10.1099/mic.0.039032-0, 039032 2010 SGM (12 pgs.).

Viadas, Cristina et al., "Transcriptome Analysis of the Brucella abortus BvrR/BvrS Two-Component Regulatory System", PLoS ONE, (www.plosone.org), Apr. 2010, vol. 5, Issue 4, e10216 (8 pgs.).

Guzman-Verri, C., "The Two-component System BvrR/BvrS essential for Brucella abortus virulence regulates the expressoin of outer membrane proteins with counterparts in members of the Rhizobiaceae", PNAS (www.pnas.org/cgi/doi/10.1073/pnas.192439399, Sep. 17, 2002, vol. 99, No. 19, pp. 12375-12380 (6 pgs.).

Pellock, Brett J. et al., "Alfalfa Root Nodule Invasion Efficiency Is Dependent on Sinorhizobium meliloti Polysaccharides", Journal of Bacteriology, Aug. 2000, vol. 182, No. 15, 0021-9193/00/$04.00+0, Copyright 2000, American Society for Microbiology, pp. 4310-4318.

Cheng, Hai-Ping et al., "Succinoglycan Is Required for initiation and Elongation of Infection Threads during Nodulation of Alfalfa by Rhizobium meliloti", Journal of Bacteriology, Oct. 1998, vol. 180, No. 19, 0021-9193/98/$04.00+0, Copyright 1998, American Society for Microbiology, pp. 5183-5191.

Cheng, Hai-Ping et al., "Succinoglycan Production by Rhizobium meliloti Is Regulated through the ExoS-Chvl Two-Component Regulatory System", Journal of Bacteriology, Jan. 1998, vol. 180, No. 1, 0021-9193/98/$04.00+0, Copyright 1998, American Society for Microbiology, pp. 20 26.

Reeve, Wayne G. et al., "Regulation of exopolysaccharide production in Rhizobium leguminosarum biovar viciae WSM710 involves exoR", Microbiology (1997), 143, 0002-1309 Copyright 1997 SGM, pp. 1951-1958, E.

(Continued)

*Primary Examiner* — Gary Nickol

*Assistant Examiner* — Khatol Shahnan Shah

(74) *Attorney, Agent, or Firm* — Peter J. Mikesell; Schmeiser, Olsen & Watts, LLP

(57) ABSTRACT

The subject matter disclosed herein pertains to the modulation of a bacterial invasion switch and the subsequent use of the bacterium to vaccinate an organism. In one embodiment, the bacterial invasion switch is modulated by changing the proteolysis of ExoR protein. In another embodiment, a mutated bacterium produces a mutant ExoR protein that resists proteolysis.

11 Claims, 11 Drawing Sheets

(56) References Cited

PUBLICATIONS

Reed, Jason W. et al., "The exoR Gene of Rhizobium meliloti Affects RNA Levels of Other exo Genes but Lacks Homology to Known Transcriptional Regulators", Journal of Bacteriology, Jun. 1991, 0021-9193/91/123789-06$02.00/0, Copyright 1991, American Society for Microbiology, pp. 3789-3794.

Doherty, Daniel et al., "Rhizobium meliloti Mutants That Overproduce the R. Meliloti Acidic Calcofluor-Binding Exopolysaccharide", Journal of Journal of Bacteriology, vol. 170, No. 9, Sep. 1988, 0021-9193/88/094249-08$02.00/0, Copyright 1988, American Society for Microbiology, pp. 4249-4256.

* cited by examiner

|     | Sequence | Overall ExoF Identity | |
|---|---|---|---|
| S.m. | TGSRWALANMYAYGDGVAENDLEAFK | 100 | SEQ ID NO. 4 |
| S.m.w. | TGSRWALANMYAYGDGVAENDLEAFK | 97 | SEQ ID NO. 5 |
| R.sp | TGSRWALANMYAYGDGVAENDLEAFK | 93 | SEQ ID NO. 6 |
| A.v. | TGSRWALANMYADGDGVVKNDYEAFK | 74 | SEQ ID NO. 7 |
| A.t. | TGSRWALANMYAYGDGVAKNDLEAFK | 73 | SEQ ID NO. 8 |
| A.r. | TGSRWALANMYADGDGVTQDDFEAFK | 71 | SEQ ID NO. 9 |
| R.l. | TGSRWALANMYADGDGVTQDDFEAFK | 70 | SEQ ID NO. 10 |
| H.p. | PGARWALANMYAYGDGVIENDYEAFK | 68 | SEQ ID NO. 11 |
| R.e. | TGSRWALANMYADGDGVAQDDFEAFK | 68 | SEQ ID NO. 12 |
| M.sp. | VGARWKLARMYAEGDGVARNDYEAFK | 54 | SEQ ID NO. 13 |
| O.i. | QGAKWKLARMYADGDGVPENDYEAYK | 54 | SEQ ID NO. 14 |
| O.a. | GGAKWKLARMYADGDGVPENDYEAYK | 52 | SEQ ID NO. 15 |
| B.a. | QGAKWKLARMYAEGDGVAEDDYEAYK | 51 | SEQ ID NO. 16 |
| B.c. | QGAKWKLARMYAEGDGVAEDDYEAYK | 51 | SEQ ID NO. 17 |
| B.o. | QGAKWKLARMYAEGDGVAEDDYEAYK | 51 | SEQ ID NO. 18 |
| B.m. | QGAKWKLARMYAEGDGVAEDDYEAYK | 51 | SEQ ID NO. 19 |

Positions 75–100; S. m. ExoR proteolysis region indicated.

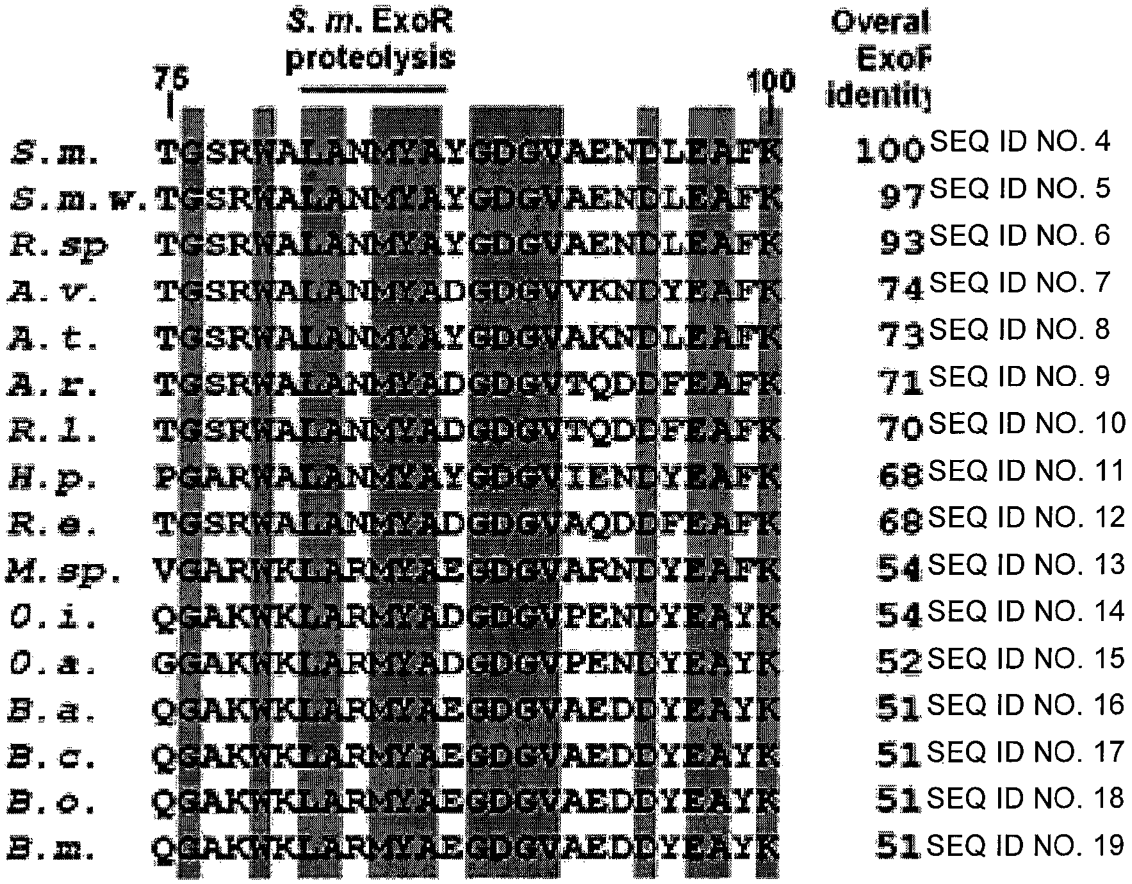

FIG. 9

FIG. 10A
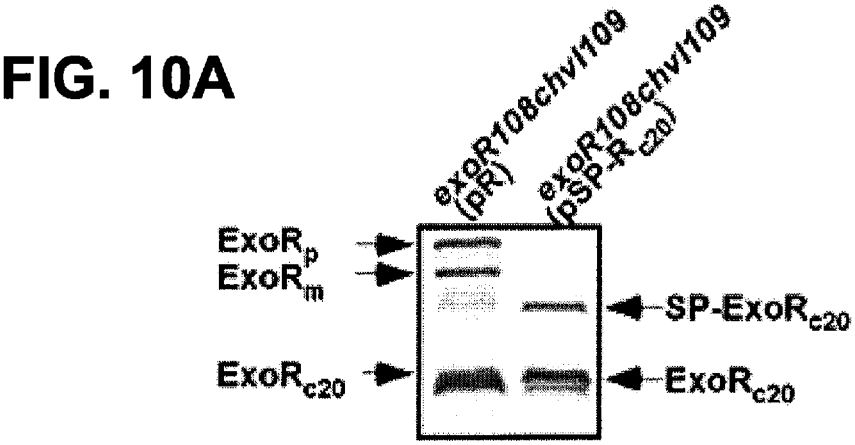
| | |
|---|---|
| Rm1021 | Rm1021 (pSP-$R_c$20) |
| *exoR95* | *exoR95* (pSP-$R_c$20) |
FIG. 10B
FIG. 10C
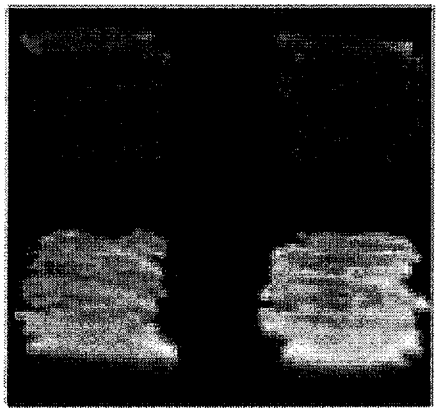
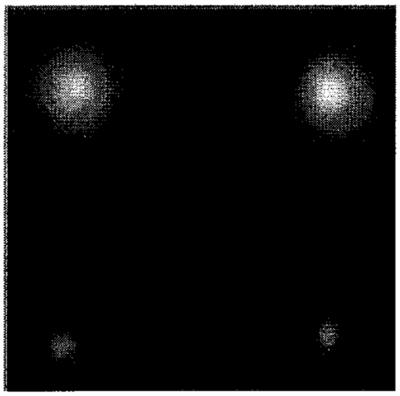
FIG. 10D FIG. 11A
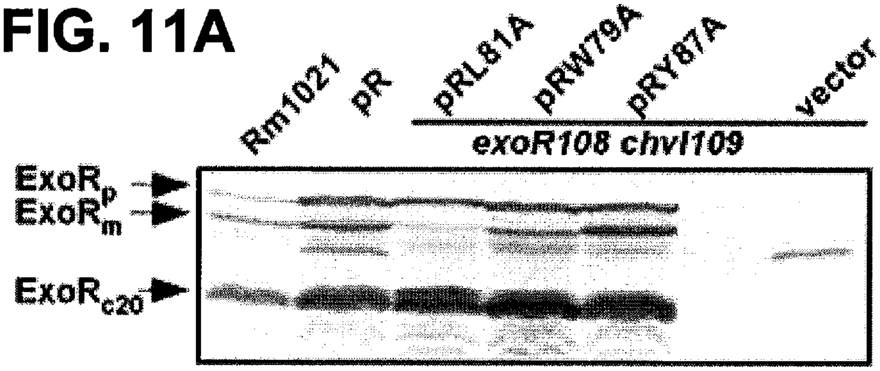
FIG. 11B
| | | |
|---|---|---|
| Rm1021 | *exoR95* | *exoY210* |
| *exoR95* (vector) | *exoR95* (p*R*) | *exoR95* (p*RL81A*) |
| *exoR95* (p*RW79A*) | *exoR95* (p*RY87A*) | |
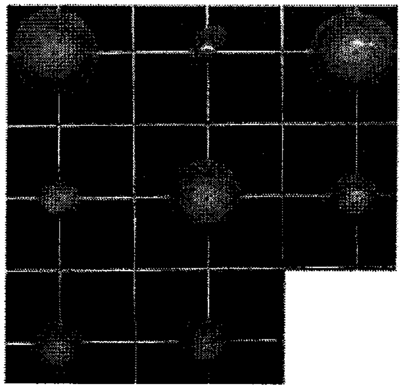
FIG. 11C
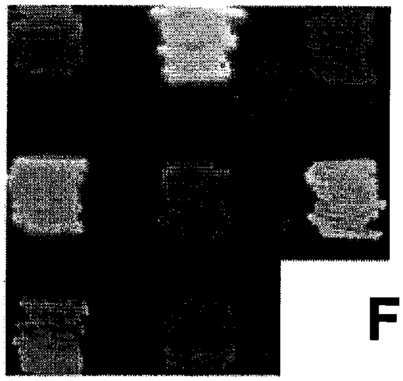
FIG. 11D

SEQUENCE LISTING

<160> NUMBER OF SEQ ID NOS: 19

<210> SEQ ID NO 1
<211> LENGTH: 26
<212> TYPE: PRT
<213> ORGANISM: Sinorhizobium meliloti

<400> SEQUENCE: 1

Thr Gly Ser Arg Trp Ala Leu Ala Asn Met Tyr Ala Tyr Gly Asp Gly
1 5 10 15

Val Ala Glu Asn Asp Leu Glu Ala Phe Lys
20 25

<210> SEQ ID NO 2
<211> LENGTH: 9
<212> TYPE: PRT
<213> ORGANISM: Sinorhizobium meliloti

<400> SEQUENCE: 2

Ala Asp Ser Tyr Thr Gln Val Ala Ser
1 5

<210> SEQ ID NO 3
<211> LENGTH: 8
<212> TYPE: PRT
<213> ORGANISM: Sinorhizobium meliloti

<400> SEQUENCE: 3

Asp Tyr Lys Asp Asp Asp Asp Lys
1 5

<210> SEQ ID NO 4
<211> LENGTH: 26
<212> TYPE: PRT
<213> ORGANISM: Sinorhizobium meliloti

<400> SEQUENCE: 4

Thr Gly Ser Arg Trp Ala Leu Ala Asn Met Tyr Ala Tyr Gly Asp Gly
1 5 10 15

Val Ala Glu Asn Asp Leu Glu Ala Phe Lys
20 25

<210> SEQ ID NO 5
<211> LENGTH: 26
<212> TYPE: PRT
<213> ORGANISM: Sinorhizobium meliloti

<400> SEQUENCE: 5

Thr Gly Ser Arg Trp Ala Leu Ala Asn Met Tyr Ala Tyr Gly Asp Gly
1 5 10 15

Val Ala Glu Asn Asp Leu Glu Ala Phe Lys
20 25

<210> SEQ ID NO 6
<211> LENGTH: 26
<212> TYPE: PRT
<213> ORGANISM: Sinorhizobium meliloti

<400> SEQUENCE: 6

Thr Gly Ser Arg Trp Ala Leu Ala Asn Met Tyr Ala Tyr Gly Asp Gly
1 5 10 15

Val Ala Glu Asn Asp Leu Glu Ala Phe Lys
20 25

<210> SEQ ID NO 7
<211> LENGTH: 26
<212> TYPE: PRT
<213> ORGANISM: Sinorhizobium meliloti

<400> SEQUENCE: 7

```
Thr Gly Ser Arg Trp Ala Leu Ala Asn Met Tyr Ala Asp Gly Asp Gly
1               5                   10                  15

Val Val Lys Asn Asp Tyr Glu Ala Phe Lys
            20                  25
```

<210> SEQ ID NO 8
<211> LENGTH: 26
<212> TYPE: PRT
<213> ORGANISM: Sinorhizobium meliloti

<400> SEQUENCE: 8

```
Thr Gly Ser Arg Trp Ala Leu Ala Asn Met Tyr Ala Tyr Gly Asp Gly
1               5                   10                  15

Val Ala Lys Asn Asp Leu Glu Ala Phe Lys
            20                  25
```

<210> SEQ ID NO 9
<211> LENGTH: 26
<212> TYPE: PRT
<213> ORGANISM: Sinorhizobium meliloti

<400> SEQUENCE: 9

```
Thr Gly Ser Arg Trp Ala Leu Ala Asn Met Tyr Ala Asp Gly Asp Gly
1               5                   10                  15

Val Thr Gln Asp Asp Phe Glu Ala Phe Lys
            20                  25
```

<210> SEQ ID NO 10
<211> LENGTH: 26
<212> TYPE: PRT
<213> ORGANISM: Sinorhizobium meliloti

<400> SEQUENCE: 10

```
Thr Gly Ser Arg Trp Ala Leu Ala Asn Met Tyr Ala Asp Gly Asp Gly
1               5                   10                  15

Val Thr Gln Asp Asp Phe Glu Ala Phe Lys
            20                  25
```

<210> SEQ ID NO 11
<211> LENGTH: 26
<212> TYPE: PRT
<213> ORGANISM: Sinorhizobium meliloti

<400> SEQUENCE: 11

```
Pro Gly Ala Arg Trp Ala Leu Ala Asn Met Tyr Ala Tyr Gly Asp Gly
1               5                   10                  15

Val Ile Glu Asn Asp Tyr Glu Ala Phe Lys
            20                  25
```

<210> SEQ ID NO 12
<211> LENGTH: 26
<212> TYPE: PRT
<213> ORGANISM: Sinorhizobium meliloti

<400> SEQUENCE: 12

-continued

```
Thr Gly Ser Arg Trp Ala Leu Ala Asn Met Tyr Ala Asp Gly Asp Gly
1               5                   10                  15

Val Ala Gln Asp Asp Phe Glu Ala Phe Lys
            20                  25


<210> SEQ ID NO 13
<211> LENGTH: 26
<212> TYPE: PRT
<213> ORGANISM: Sinorhizobium meliloti

<400> SEQUENCE: 13

Val Gly Ala Arg Trp Lys Leu Ala Arg Met Tyr Ala Glu Gly Asp Gly
1               5                   10                  15

Val Ala Arg Asn Asp Tyr Glu Ala Phe Lys
            20                  25


<210> SEQ ID NO 14
<211> LENGTH: 26
<212> TYPE: PRT
<213> ORGANISM: Sinorhizobium meliloti

<400> SEQUENCE: 14

Gln Gly Ala Lys Trp Lys Leu Ala Arg Met Tyr Ala Asp Gly Asp Gly
1               5                   10                  15

Val Pro Glu Asn Asp Tyr Glu Ala Tyr Lys
            20                  25


<210> SEQ ID NO 15
<211> LENGTH: 26
<212> TYPE: PRT
<213> ORGANISM: Sinorhizobium meliloti

<400> SEQUENCE: 15

Gly Gly Ala Lys Trp Lys Leu Ala Arg Met Tyr Ala Asp Gly Asp Gly
1               5                   10                  15

Val Pro Glu Asn Asp Tyr Glu Ala Tyr Lys
            20                  25


<210> SEQ ID NO 16
<211> LENGTH: 26
<212> TYPE: PRT
<213> ORGANISM: Sinorhizobium meliloti

<400> SEQUENCE: 16

Gln Gly Ala Lys Trp Lys Leu Ala Arg Met Tyr Ala Glu Gly Asp Gly
1               5                   10                  15

Val Ala Glu Asp Asp Tyr Glu Ala Tyr Lys
            20                  25


<210> SEQ ID NO 17
<211> LENGTH: 26
<212> TYPE: PRT
<213> ORGANISM: Sinorhizobium meliloti

<400> SEQUENCE: 17

Gln Gly Ala Lys Trp Lys Leu Ala Arg Met Tyr Ala Glu Gly Asp Gly
1               5                   10                  15

Val Ala Glu Asp Asp Tyr Glu Ala Tyr Lys
            20                  25


<210> SEQ ID NO 18
<211> LENGTH: 26
```

-continued

```
<212> TYPE: PRT
<213> ORGANISM: Sinorhizobium meliloti

<400> SEQUENCE: 18

Gln Gly Ala Lys Trp Lys Leu Ala Arg Met Tyr Ala Glu Gly Asp Gly
1               5                   10                  15

Val Ala Glu Asp Asp Tyr Glu Ala Tyr Lys
            20                  25


<210> SEQ ID NO 19
<211> LENGTH: 26
<212> TYPE: PRT
<213> ORGANISM: Sinorhizobium meliloti

<400> SEQUENCE: 19

Gln Gly Ala Lys Trp Lys Leu Ala Arg Met Tyr Ala Glu Gly Asp Gly
1               5                   10                  15

Val Ala Glu Asp Asp Tyr Glu Ala Tyr Lys
            20                  25
```

METHOD FOR MODULATING A BACTERIAL INVASION SWITCH

STATEMENT OF FEDERALLY SPONSORED RESEARCH OR DEVELOPMENT

This invention was made with Government support under Contract Nos. 5SC3GM081147-05 and SGM081147A awarded by the National Institute of Health (NIH). The government has certain rights in the invention.

CROSS-REFERENCE TO RELATED APPLICATIONS

This application is a non-provisional of U.S. Patent Application Ser. No. 61/652,120 (filed May 25, 2012), the entirety of which is incorporated herein by reference.

BACKGROUND OF THE INVENTION

The subject matter disclosed herein relates to a method of modulating a bacterial invasion switch and the subsequent use of the treated bacterium to vaccinate an organism.

BRIEF DESCRIPTION OF THE INVENTION

In one embodiment, the disclosure pertains to a method for modulating a bacterial invasion switch by changing the proteolysis of ExoR protein. The method comprises a steps of administering a protease inhibitor to a bacterium which changes proteolysis of ExoR to modulate an invasion switch of the bacterium, thereby keeping the bacterium in a non-pathogenic. A first ExoR level is determined after the step of administering wherein the first ExoR level is lower than a second ExoR level prior to the step of administering.

In another embodiment, the disclosure pertains to a method for immunizing an organism by introducing a mutated bacterium to the organism. The bacterium has a bacterial invasion switch that has been modulated by changing the proteolysis of ExoR protein. The method comprises making a mutant bacterium wherein the mutant bacterium produces a mutated $ExoR_m$ protein that is resistant to proteolysis relative to a wild-type bacterium thereby placing the bacterium in a non-pathogenic state. The mutant bacterium is introduced to an organism and the organism is permitted an opportunity to produce an immune response to the mutant bacterium.

An advantage that may be realized in the practice of some disclosed embodiments of the method is that the organism has the opportunity to produce an immune response to a whole body bacterium.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 9 shows amino acid sequence alignment of ExoR proteolysis regions from 16 ExoR orthologs. Conserved amino acids are shaded. The overall amino acid identities between *S. meliloti* ExoR and its orthologs are listed. The positions of the amino acids and the site of proteolysis are marked based on *S. meliloti* ExoR protein. The following species are shown: S. m. (*S. meliloti* Rm1021), S.m.w. (*Sinorhizobium medicae* WSM419), R. sp. (*Rhizobium* sp. NGR234), A. v. (*Agrobacterium vitis* S4), A. t. (*Agrobacterium tumefaciens* str. C58), A. r. (*Agrobacterium radiobacter* $K_{84}$), R. l. (*Rhizobium leguminosarum* bv. *trifolii* WSM2304), H p. (*Heoflea phototropica* DFL-43), R. e. (*Rhizobium etli* CIAT652), M sp. (*Mesorhizobium* sp. BNC1), 0.1. (*Ochrobactrum intermedium* LMG 3301), O. a. (*Ochrobactrum anthropi* ATCC 49188). B. a. (*Brucella abortus* str. 2308 A), B. c. (*Brucella ceti* str. Cudo), B. o. (*Brucella ovis* ATCC 25840), and B. m. (*Brucella melitensis* 16M);

FIGS. 10A, 10B, 10C and 10D are a biochemical and functional analysis of ExoR proteolysis product $ExoR_{c20}$, which was expressed from pHC510 (pR) and pHC567 (pSP-$R_{c20}$) in the exoR108chvI109 mutant for ExoR and SP-ExoR, and probed in western blot (10A). The effects the presence of $ExoR_{c20}$ on succinoglycan production was measured by calcofluor fluorescence (10B and 10C) and its effects on swimming ability was measured by the size of the colonies (10D);

FIGS. 11A, 11B, 11C and 11D are a biochemical and functional analysis of ExoR proteins with single amino acid mutations, ExoRL81A, ExoRW79A, and ExoRY87A, expressed from plasmids pHC571, pHC572, and pHC573, respectively, in the exoR108chvI109 mutant for western blot (A), and in the exoR95 mutant for their effects on succinoglycan production (B and C) and swimming ability (D)

DETAILED DESCRIPTION OF THE INVENTION

To conserve biological energy, bacteria maintain one of two states: a free-living (non-pathogenic) state or an infective (pathogenic) state. Each of these states are characterized by certain genes being activated or deactivated. Generally, when a bacteria is in an environment that is less suitable for replication (e.g. on a non-living or infection resistant surface) the bacteria in the free-living state. When the bacteria is in an environment that is more suitable for replication (e.g. within a host organism) the bacteria changes to the infective state. A signaling mechanism must be present that permits the bacteria to sense its environment and selectively enter one of these states, however, the nature of this signaling mechanism is not known. Disclosed in this specification are details of such a signaling mechanism and a method that utilizes this newly discovered mechanism to maintain a bacteria in a free-living (non-pathogenic) state.

Figure 1:
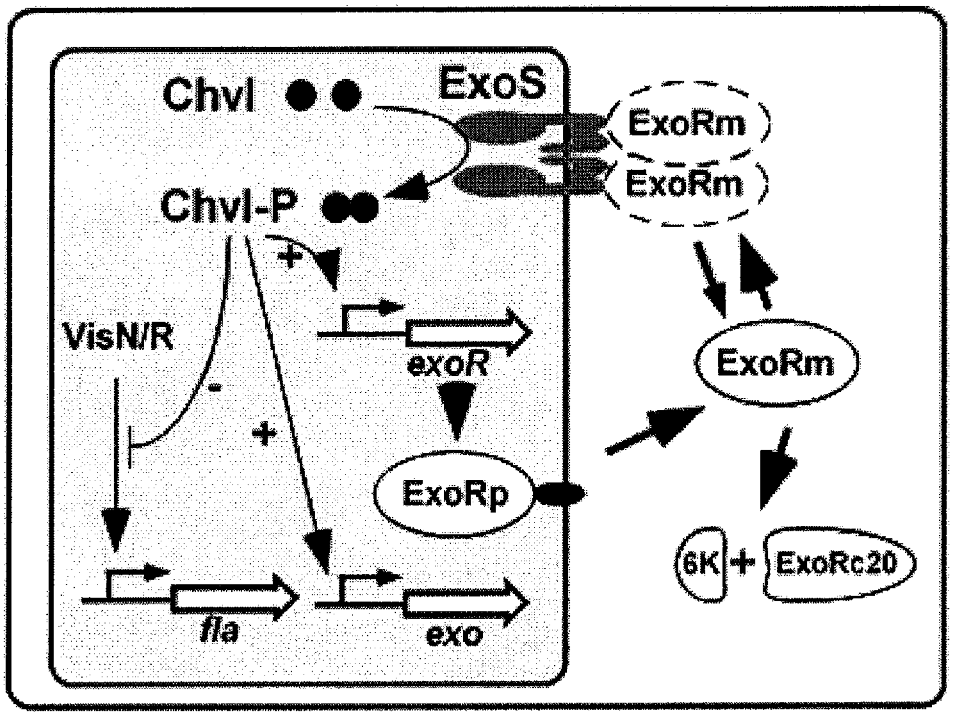
FIG. 1 is a depiction of a signal sensing pathway for a bacteria utilizing three proteins: ExoR, ExoS and ChvI.

FIG. 1 is a depiction of a signal sensing pathway for a bacteria utilizing three proteins: ExoR, ExoS and ChvI. Without wishing to be bound to any particular theory, ChvI is thought to form a signal pathway with ExoS. ExoS, in turn, forms a complex with ExoR. To the extent the ExoS/ExoR complex is predominant, the free-living (non-pathogenic) state is favored. Conversely, reduction in the level of ExoS/ExoR complex produces a corresponding increase in the level of infective (pathogenic) bacteria. The degree to which the ExoS/ExoR complex is formed is controlled, at least in part, by the concentration of free ExoR. ExoR has been found to exist in two states: an $ExoR_p$ (precursor, 29 kD) that is found in the cytoplasm and $ExoR_m$ (mature, 26 kD) that is found in the periplasmic space between the inner and outer membranes. It is believed $ExoR_m$ is the form of the protein that binds with ExoS in the periplasmic space to maintain the bacteria in a free-living (non-pathogenic) state. It is further believed there is an equilibrium between the bound ExoS/$ExoR_m$ complex and the free $ExoR_m$ state and that this equilibrium is the signaling mechanism that switches the bacteria between free-living and infectious states. Specifically, the $ExoR_m$ (26 kD) is subjected to proteolysis to yield a 6 kD fragment and an $ExoR_{c20}$ (20 kD) fragment. This proteolysis shifts the equilibrium toward the free $ExoR_m$ state which reduces the ExoS/ExoR complex and thereby favors the infectious state. Environmental factors, including high salt concentration, have been found to facilitate the proteolysis of $ExoR_m$. This explains why, upon exposure to the relatively high-salt environment of a host, the bacteria are rendered pathogenic.

In one embodiment, a method is provided for inhibiting the proteolysis of $ExoR_m$. Such a method disrupts the bacteria's ability to disassociate the ExoS/ExoR complex and thereby locks the bacteria into a free-living (non-pathogenic) state. For example, a protease inhibitor may be used to reduce or halt the proteolysis of $ExoR_m$. In another example, a bacteria is produced with a mutated exoR gene which, in turn, produces an $ExoR_m$ variant that is resistant to proteolysis. Such a bacteria may be introduced into a host so as to permit the host the opportunity to produce an immune response without risking the bacteria becoming pathogenic. This provides an alternative mechanism to vaccinate the host. One such exemplary method is depicted in FIG. 2.

Figure 2:
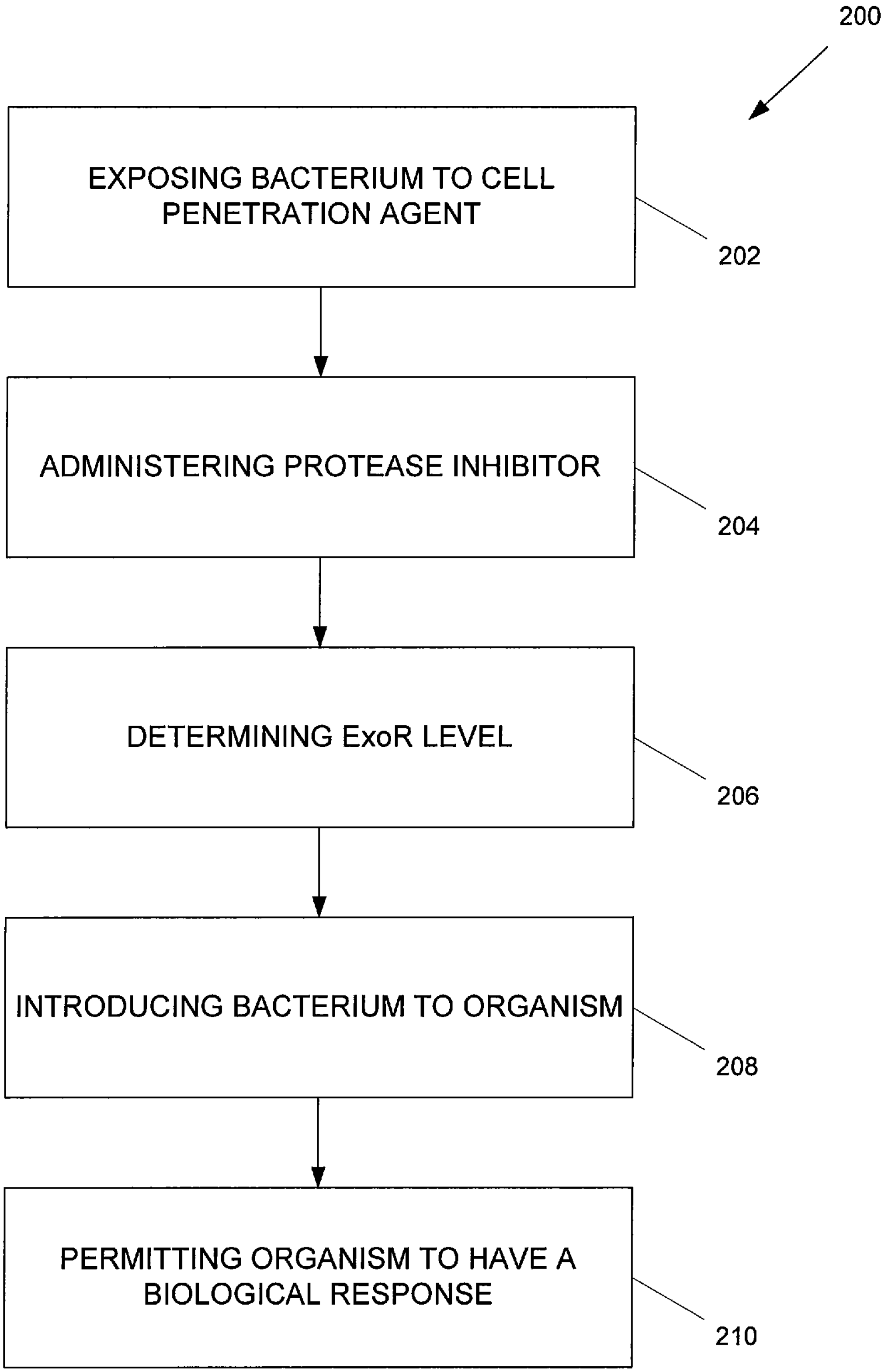
FIG. 2 is a flow diagram depicting an exemplary method for modulating a bacterial invasion switch by changing the proteolysis of ExoR protein.

FIG. 2 is a flow diagram depicting an exemplary method 200 for modulating a bacterial invasion switch by changing the proteolysis of ExoR protein. In some embodiments, the method 200 comprises a step 202 of exposing a bacterium to a cell penetration agent. In one embodiment, the cell penetration agent is a detergent known to increase the permeability of cellular membranes. In one such embodiment, the detergent is sodium dodecyl sulfate (SDS). In another embodiment, the cell penetration agent is a cell-penetrating peptide.

The method 200 further comprises a step 204 of administering a protease inhibitor to the bacterium which changes proteolysis of ExoR to modulate an invasion switch of the bacterium. This lack of proteolysis has the effect of keeping the bacterium in a non-pathogenic state. Specifically, the ExoR form that is changed or prevented from undergoing proteolysis is the mature form, $ExoR_m$. In one embodiment, the protease inhibitor is phenylmethylsulfonyl fluoride (PMSF). In one embodiment, the protease inhibitor is selected to permeate a cellular membrane such that it resides in the periplasmic space between two adjacent membranes. For example, the protease inhibitor may be a non-protein molecule with a molecular weight of less than about three hundred grams per mole. Additional examples of such protease inhibitors are known in the art.

The method 200 further comprises a step 206 of determining a first ExoR level after the step of administering wherein the first ExoR level is lower than a second ExoR level prior to the step of administering. Specifically, the ExoR form that is determined is the mature form, $ExoR_m$. In one embodiment, step 206 comprises testing the bacterium to verify an ability of the bacterium to invade an organism. If the bacterium's ability to invade is comprised, relative to an untreated bacterium, then the first ExoR levels have been determined to be lowered by method. Such an ability to invade can be determined by conventional techniques including, but not limited to, simple microscopy of a macrophage, detection of an immune response (or other biological response including symbiosis) of the organism.

The method 200 further comprises a step 208 of introducing the bacterium to an organism and, in step 210, permitting the organism an opportunity to produce an immune response. In one embodiment, the organism is an animal. In another embodiment, the organism is a plant. Examples of methods of introduction include oral administration, injection, topical application, and the like. In one embodiment, the step 208 is only performed after step 206 has been completed and the bacterium has been confirmed as being successfully modified. The particular bacterium utilized in step 208 are from the same bacteria sample as the bacterium utilized in step 206. By being introduced to the full bacterium while it is in a non-pathogenic state, the organism has the opportunity to produce antibodies corresponding to the full surface of the bacterium. In contrast, current vaccines are typically made from very few proteins or surface molecules of bacteria, which means only small areas of bacterial cells can be recognized by our immune systems. The disclosed method presents the whole body bacteria to provide a superior immunization method.

Figure 3:
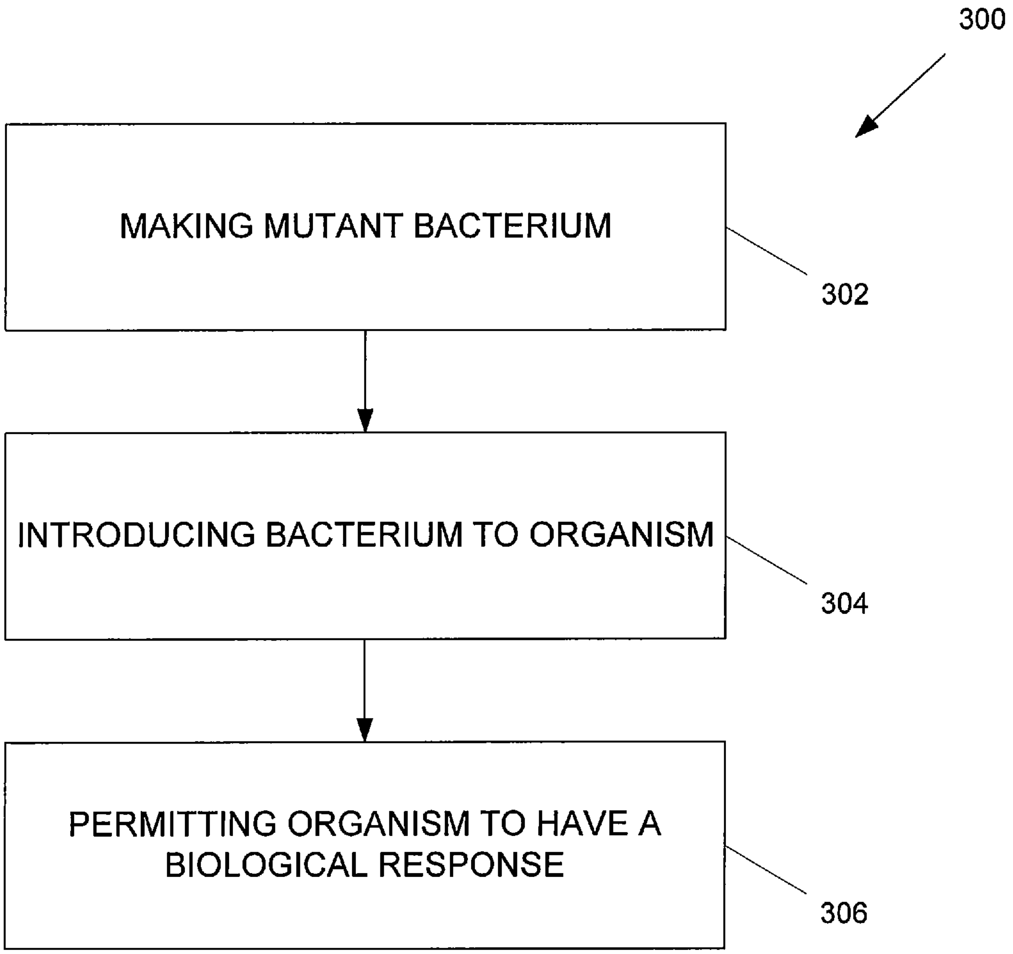
FIG. 3 is a flow diagram depicting an exemplary method for immunizing an organism by introducing a mutated bacterium to the organism.

FIG. 3 is a flow diagram depicting an exemplary method 300 for immunizing an organism by introducing a mutated bacterium to the organism. The method 300 comprises a step 302 of making a mutant bacterium wherein the mutant bacterium produces a mutated $ExoR_m$ protein that is resistant to proteolysis relative to a wild-type bacterium. Such a mutated bacterium is locked in a non-pathogenic state. Methods of making such a mutant are known to those skill in the art. For example, mutations can be induced using polymerase chain reaction (PCR) techniques or by random chemical mutagenesis. Once mutations are induced, the resulting bacteria can be screened to isolate mutated strains of the ExoR protein.

The method 300 further comprises a step 304 of introducing the mutant bacterium to an organism and, in step 306, permitting the organism an opportunity to produce an immune response to the mutant bacterium. The steps 304 and 306 parallel the steps 208 and 210 of method 200.

In one embodiment, the method is used to promote plant growth with increased nitrogen fixing symbiosis. The growth of a plant is limited by the availability of nitrogen. While most plants will stop growing in the absent of adequate nitrogen nutrient, the plants in the legume family, including all the bean and pea producing plants, establish symbiosis with nitrogen fixing bacteria. Changing the structure of the invasion switch component can increase nitrogen fixing symbiosis thus more plant growth and more food production. The method may also be used to expand farming to areas to dry or too salty to grow crop. Changing invasion switch components can raise dry and salt tolerance of during the establishment of nitrogen fixing symbiosis. For example, salts were found to be the signal for the invasion switch by plant symbiont, *S. meliloti*, plant pathogen *Agrobacterium tumefaciens*, and animal pathogen *Brucella abortus*. This group of bacteria have evolved to use salts secreted by hosts including human and animals as the signals to turn into pathogenic bacteria to be more effective in invading hosts.

In another embodiment, the method is used in agriculture including preventing bacterial infection of plants especially the broad host range pathogen *Agrobacterium tumefaciens*. Blocking the sensing function of RSI invasion switch in this bacterium will prevent it from turning into pathogen and infect crop plants Studies Pertaining to ExoR Proteolysis To understand how ExoR suppression of ExoS is relieved which is required for the expression of ExoS/ChvI regulated symbiosis genes, wild-type ExoR and ExoR95 mutant proteins were characterized. In addition to the previously identified precursor and mature forms of ExoR (designated $ExoR_p$ and $ExoR_m$, respectively), a 20-kD form of ExoR (designated $ExoR_{c20}$) was detected that is derived from the wild-type ExoR protein but not from the ExoR95 mutant protein. $ExoR_{c20}$ was isolated directly from *S. meliloti* periplasm to identify its N-terminal amino acids and the site of the proteolysis, which is highly conserved among ExoR homologs. $ExoR_{c20}$ retains the C-terminus of the wild type ExoR. When expressed directly, $ExoR_{c20}$ did not complement the exoR95 mutation, suggesting that $ExoR_{c20}$ does not function directly in the ExoR-ExoS/ChvI regulatory pathway and that $ExoR_m$ is the functional form of ExoR. A single amino acid change (ExoRL81A) at the site of ExoR periplasmic proteolysis resulted in the reduction of the amount of $ExoR_m$ and the loss of the regulatory function of the ExoR protein. These findings suggest that $ExoR_m$ is a target of periplasmic proteolysis and that the amount of $ExoR_m$ could be reduced through an effective proteolysis to release its suppression of ExoS. Further details may be found in provisional patent application 61/652,120, the content of which is incorporated by reference.

The Gram-negative soil bacterium *Sinorhizobium meliloti* establishes a nitrogen-fixing symbiosis with its plant host alfalfa (*Medicago sativa*) through a set of complex and reciprocal signal exchanges in the absence of fixed nitrogen sources. The formation of an infection thread inside alfalfa root hairs is an essential step in the early stage of this symbiosis that requires the presence of *S. meliloti* exopolysaccharides, succinoglycan (SG), EPSII, or capsular polysaccharide (KPS). *S. meliloti* succinoglycan (SG) has been shown to be much more effective than the other two *S. meliloti* polysaccharides, exopolysaccharide II (EPS II) and capsular polysaccharide (KPS), at eliciting the formation of infection threads. The structure and biosynthetic pathway of succinoglycan have been well documented although its precise role in eliciting the formation of infection threads remains unknown.

Succinoglycan production is inversely co-regulated with flagellum production by a single signal-transduction pathway consisting of the *S. meliloti* ExoR protein and the ExoS/ChvI two-component regulatory system and the EmmABC system. While the transcription of succinoglycan biosynthesis genes is upregulated by mutations exoR95::Tn5 and exoS96::Tn5, transcription of the flagellum biosynthesis genes is down-regulated. This coordinated regulation is consistent with the switch from free-living to invasion-ready cells that is required at this stage of the symbiosis. It also suggests that the ExoR protein and the ExoS/ChvI two-component system play crucial roles in controlling the overall changes needed for *S. meliloti* cells to switch from free living to symbiosis inside the root nodules.

The *S. meliloti* exoR gene was initially identified through isolation of the exoR95::Tn5 mutation, which was later identified and sequenced. The exoR gene encodes a 268-amino acid ExoR protein with a conserved signal peptide for exporting the protein to the bacterial periplasm, as confirmed in recent findings. In addition to regulating succinoglycan and flagellum production, ExoR has been shown to be involved in regulating biofilm production and lipopolysaccharide modifications. The ExoR protein has been found to regulate the expression of a large number of gene functions in very different metabolic pathways, suggesting that ExoR plays other important roles. ExoR homologs have been found and characterized in *Rhizobium leguminosarum* and *Agrobacterium tumefaciens*, where they also function in regulating polysaccharide, flagellum, and biofilm production. Many additional ExoR homologs have been discovered in recent genome-sequencing efforts, but little is known about their function.

The *S. meliloti* ExoS and ChvI proteins form a typical bacterial two-component signal-transduction system. The *S. meliloti* ExoS protein consists of a large periplasmic domain and a cytoplasmic kinase domain, and it has been shown to phosphorylate *S. meliloti* ChvI directly. Recent analysis of exoS- and chvI-deletion mutants has shown that the ExoS/ChvI system is essential for symbiosis and that these two proteins regulate the expression of a variety of genes involved in carbon metabolism and many other functions. These findings are consistent with the results of a transcriptome analysis of the exoS96 mutant. Collectively, these findings suggest that the ExoS/ChvI system plays an essential role in preparing *S. meliloti* cells for their transformation from free living to nitrogen-fixing cells inside the root nodules. The importance of the *S. meliloti* ExoS/ChvI system was further highlighted by the finding that two of its close homologs are essential for host infections in *Brucella abortus* and *A. tumefaciens*.

Recent genetic and biochemical data suggest that ExoR, ExoS, and ChvI form a single signal-transduction pathway. The ExoR protein has been localized to the periplasm of *S. meliloti* cells, and as confirmed by our unpublished data. ExoR has been found to exist in two forms, the 29-kD full-length precursor form ($ExoR_p$) and the 26-kD mature form without its predicted signal peptide ($ExoR_m$) in wild-type *S. meliloti* cells. Co-immunoprecipitation of ExoR and ExoS suggested that they form protein complexes. Increased expression of the exoS gene also led to accumulation of $ExoR_m$, suggesting that ExoS stabilizes ExoR in the ExoR-ExoS complex. The ExoR-ExoS interaction was interrupted by single amino acid changes in either the ExoR protein or the periplasmic domain of ExoS. Taken together, these findings led to a proposed model in which ExoR interacts with ExoS to form a protein complex that keeps the ExoS in the off state, resulting in conditions favoring free living, with higher levels of flagellum production and lower levels of succinoglycan production.

Expanding on this suggested model, our recent data from genetic analyses suggest that ExoR autoregulates its own expression through the ExoS/ChvI two-component system. Loss of functional ExoR protein in the exoR95 mutant leads to upregulation of exoR gene expression, along with that of succinoglycan biosynthetic genes. This upregulation can be suppressed by single amino acid mutations in the ExoS sensing domain, which is consistent with direct ExoR-ExoS interactions. This raises the possibility that ExoR autoregulation through the ExoS/ChvI system is used to modulate the expression of the genes regulated by the ExoS/ChvI system in response to host or environmental signals.

While current model can explain how ExoR turns off the ExoS/ChvI system, it does not explain how the ExoS/ChvI system is turned on during symbiosis in response to environmental or plant signals. Our new findings, presented herein, provide a better understanding of the molecular basis for ExoR protein's ability to turn the ExoS/ChvI two-component regulatory system on and off.

Materials and Methods

Strains, Plasmids and Media

The strains, phage and plasmids used in this study are listed in Table 1 of U.S. provisional patent application 61/652,120. *Escherichia coli* strains were grown in Luria-Bertani (LB) medium at 37° C. and *Sinorhizobium meliloti* strains were grown in LB medium supplemented with 2.5 mM $MgSO_4$ and 2.5 mM $CaCl_2$ (LB/MC) at 30° C. (29). LB/MC agar containing 0.02% (w/v) calcofluor white M2R (Blue Brighter 28, Sigma) was buffered to pH 7.4 with 10 mM HEPES (N-2-hydroxyethylpiperazine-N-2-ethanesulfonic acid) and used to examine succinoglycan production on agar media. The following antibiotics were used at the concentrations indicated: ampicillin, 100 $\mu ml^{-1}$; chloramphenicol, 10 $\mu g\ ml^{-1}$; neomycin, 200 $\mu ml^{-1}$; kanamycin, 25 $\mu g\ ml^{-1}$; spectinomycin, 100 $\mu g\ ml^{-1}$; tetracycline, 10 $\mu ml^{-1}$, and streptomycin, 500 $\mu g\ ml^{-1}$.

Motility Assay

Bacterial cell motility was examined using swarming plates containing 0.3% agar as described previously with some modifications. Briefly, fresh cell cultures were prepared and diluted to OD600 of 0.1. Then 2 μL of each diluted culture was inoculated into LB/MC soft agar plate and incubated for 2-3 days to determine colony size.

Plant Nodulation Test

Alfalfa nodulation assays were carried out on plates as previously described with slight modifications. A set of eight alfalfa seedlings were planted in a square Petri dish and all plants were grown inside the Petri dishes. Plants were examined after 4 weeks for number of nodules to determine overall symbiotic efficiency.

Expression and Purification of *S. Meliloti* ExoR-his for Antibody Production The *S. meliloti* exoR ORF was obtained by PCR using Rm1021 genomic DNA as the template and two PCR primers: exoRfNdeI-1 exoRrXhoI-1. The PCR product was digested with NdeI and XhoI, and then cloned into pET-16b between restriction sites NdeI and XhoI to generate plasmid pHC615. The His-tagged ExoR protein was purified from BL21DE3 (plysS, pHC615) with 1 mM IPTG (Isopropyl β-D-1-thiogalactopyranoside) induction and using a Ni-NTA purification system under denaturing conditions (Invitrogen). Purification of the His-tagged ExoR protein was confirmed using Coomassie blue-stained SDS-polyacrylamide gels and sent to Pacific Immunology Company (Ramona, Calif.) to raise ExoR-specific polyclonal antibodies in rabbits. The specificity of the ExoR-specific polyclonal antibodies was confirmed by western blot.

Immunoblotting

For immunoblotting, total cellular proteins or purified protein were resolved by SDS-PAGE, transferred to a PVDF (Polyvinylidene fluoride) membrane (Bio-Rad), detected with primary antibodies including ExoR-specific polyclonal antibodies and FLAG-specific monoclonal antibody coupled with alkaline phosphatase (AP) (Novagen), and treated with NBT/BCIP (nitro-blue tetrazolium and 5-bromo-4-chloro-3'-indolyphosphate) (Sigma) to detect AP activities.

Construction of the exoR108chvI109 Double Mutant

The DNA fragment consisting of nucleotide 88 to 433 of the exoR ORF was generated by PCR using *S. meliloti* Rm1021 genomic DNA as the template and two PCR primers: exoRdfHindIII-2 and exoRdrBsrGI. The PCR product was digested with HindIII and BsrGI, and cloned into suicide plasmid pK19mob2ΩHMB to produce pHC508. The resulting plasmid was then conjugated into *S. meliloti* Rm1021 using helper MT616 in a triparental mating and a few conjugants were isolated after 6 days. The interrupted exoR gene was transduced from the conjugants to Rm1021, which yielded only one transductant, the exoR108 mutant. Insertion of the suicide plasmid into the genome was confirmed by PCR and sequencing the site of insertion. The chvI gene was amplified from the genome of the exoR108 transductant using primers chvIf-27 and chvIr759, and sequenced using primers chvIf293 and chvIr419. The exoS gene was similarly amplified from the genome of the exoR108 transductant using primers exoSf-61 and exoSr1918, and sequenced using primers exoSr407, exoSr829, exoSf653, exoSf1098 and exoSr1912. One single mutation was found in the chvI gene but no mutations were found in the exoS gene. The exoR108 transductant was thus designated exoR108chvI109 double mutant. The construct was confirmed by sequencing. The primers used in cloning and sequencing are listed in Table 2 in U.S. provisional patent application 61/652,120 along with all other plasmid constructions described in this paper.

Constructs Expressing ExoR and ExoR without Signal Peptide

The DNA fragment containing the exoR promoter and ORF was generated in a PCR using *S. meliloti* genomic DNA as the template and primers exoRfHindIII-1 and exoRrXhoI-2, and cloned in between the HindIII and XhoI sites of a medium copy number plasmid pMB393 to generate pHC510. Similarly, the exoR gene was amplified by PCR using primers exoRfNdeI-3 and exoRrXhoI-3, and cloned into pHC93 to generate pHC518, expressing the wild-type ExoR from the lac promoter on the plasmid. The region of the exoR gene without the signal sequence was amplified using primers exoRfNdeI-2 and exoRrXhoI-3, cloned into plasmid pHC93 to generate pHC641, and used to express ExoRm, the form of ExoR lacking its signal peptide.

Construction and Analysis of ExoR-PhoA Fusions

A set of three ExoR-PhoA fusions were constructed. To construct the fusion of PhoA with the full-length ExoR, an XbaI/KpnI DNA fragment containing the *E. coli* phoA gene (lacking its signal sequence) was prepared by PCR using the genomic DNA of the *S. meliloti* exoF265::TnphoA mutant as the template and primers phoAfXbaI and phoArKpnI. An XhoI/XbaI DNA fragment containing the complete exoR ORF except the stop codon was obtained by PCR using *S. meliloti* Rm1021 genomic DNA as the template and two PCR primers: exoRfXhoI and exoRrXbaI. The two DNA fragments were individually treated with either XhoI/XbaI or XbaI/KpnI, and ligated with XhoI- and KpnI treated a low copy number plasmid pSW213 to generate pHC528. To construct the fusion of PhoA and ExoR without signal peptide, the region of the ExoR-PhoA fusion in pHC528 was amplified without the ExoR signal peptide region using two primers, exoRmfXhoI and phoArKpnI, and recloned into the same region of pSW213 to create pHC555. To create the fusion of PhoA with ExoR signal peptide, the coding region of the ExoR signal peptide was amplified in a PCR using pHC528 as the template and primers exoRfXhoI and exoRsp-phoAr. The region for PhoA was amplified using primers exoRsp-phoAf and phoArKpnI. The two fragments were joined together in an overlapping PCR using primers exoRfXhoI and phoArKpnI. The product of this overlapping PCR was cloned into pSW213 to create pHC533. All three fusions were expressed from an inducible lac promoter on the plasmid with 0.8 mM IPTG.

Construction and Analysis of FLAG-Tagged ExoR Proteins

The unique 8-amino acid FLAG tag (available from Sigma and described in provisional patent application 61/652,120) was inserted into the C terminus of the ExoR protein to help track it. To construct the C-terminal-tagged ExoR, ExoR-CF, a DNA fragment containing ExoR and the FLAG tag was generated by PCR using *S. meliloti* genomic DNA as the template and primers exoRfHindIII-1 and exoRcflagrXhoI, which introduced the FLAG tag. This DNA fragment was cloned into pMB393 to generate pHC630 and express ExoR-CF.

To track FLAG-tagged ExoR proteins, cells of *S. meliloti* strains expressing ExoR-CF fusion were collected from exponential-phase cultures, washed with CoIP buffer (36), and resuspended in 3 ml CoIP buffer with 1% (w/v) Triton X-100, 10 mM $MgCl_2$, 30 mg lysozyme and 30 units of DNAse I at 4° C. for 30 min, and sonicated (550 Sonic Dismembrator, Fisher Scientific) twice on ice (Level 2, 4.5 min each time). Cell lysates were centrifuged at 4° C., 13,000 rpm in a microcentrifuge for 5 min. Supernatants were collected, mixed with 20 μl anti-FLAG M2-agarose (Sigma), and incubated overnight at 4° C. The M2-agarose was collected from the reaction mixture by centrifugation at 5,000 rpm, 4° C. for 3 min, washed three times with CoIP washing buffer, resuspended in 75 μl of 100 ng $\mu l^{-1}$ FLAG peptide, incubated at 4° C. for 1 h, and centrifuged at 13,000 rpm for 5 min to collect the supernatant for storage at −20° C. Alternatively, the washed M2-agarose was mixed with 75 μl loading buffer, boiled at 100° C. for 5 min and stored at −20° C.

Direct Isolation of FLAG-Tagged $ExoR_{c20}$-CF from *S. Meliloti* Periplasm

Overnight culture of *S. meliloti* exoR95 (pHC630) was diluted 1:100 in 1 liter of fresh LB/MC/spectinomycin, and further incubated at 30° C. with shaking to an $OD_{600}$ of 0.3. Cells were collected, washed twice in TBS (20 mM Tris, 0.2 mM NaCl, pH 7.5), resuspended in TBS with 0.5 M sorbitol for 10 min at room temperature, collected by centrifugation, resuspended in sterile water for 10 min on ice, and removed by two consecutive centrifugations (10 min each, 13,000 rpm). The cell-free supernatant was mixed with HEPES buffer (40 mM HEPES, 500 mM NaCl, 4% Triton X-100, pH 7.0), mixed with 60 μl agarose beads covalently linked to FLAG-specific monoclonal antibody (Sigma A2220) following the manufacturer's instructions, and incubated at 4° C. overnight with gentle inversion of the microcentrifuge tube. Agarose beads were collected at 10,000 rpm for 1 min, washed six times with TBS buffer (50 mM Tris, 0.2 mM NaCl, pH 7.5), rinsed once with 0.5 ml 0.1M glycine-HCl (pH 3.5), resuspended in 30 μl SDS-PAGE loading buffer, boiled for 5 min, and run on a 15% SDS-polyacrylamide gel at constant 150 V for 1.5 h using the Bio-Rad gel system.

Protein N-Terminal Determinations by MS-Based Peptide Mapping

In-gel digestion of excised gel bands. Following visualization of the gel, the protein band of interest was excised and placed into a 0.5-ml microtube for subsequent in-gel digestion with trypsin and manual extraction, both performed following a protocol from. All gel-extracted supernatants were combined and evaporated to dryness in a Speedvac.

Protein identification and peptide mapping by nanoLC/MS/MS analysis. The trypsin-digested samples were reconstituted in 15 μl of 0.1% (v/v) formic acid with 2% (v/v) acetonitrile prior to MS analysis. NanoLC was carried out in an LC Packings Ultimate integrated capillary HPLC system equipped with a Switchos valve switching unit (Dionex, Sunnyvale, Calif.). The gel-extracted peptides were injected using a Famous auto sampler onto a C18 PepMap trap column for on-line desalting, and then separated on a PepMap C-18 RP nano column, eluted in a 60-min gradient of 5% to 40% acetonitrile in 0.1% formic acid at 275 nl $min^{-1}$. The nanoLC was connected in-line to a hybrid triple quadrupole linear ion trap mass spectrometer, 4000 Q Trap from ABI/MDS Sciex (Farmingham, Mass.), equipped with Micro Ion Spray Head II ion source.

Data acquisition from the MS was performed using Analyst 1.4.2 software (Applied Biosystems) in positive ion mode for information-dependent acquisition (IDA) analysis. For the IDA analysis, after each survey scan from m/z 375 to m/z 1550 and an enhanced resolution scan, the three highest-intensity ions with multiple charge states were selected for tandem MS (MS/MS) with rolling collision energy applied for detected ions based on different charge states and m/z values.

Data analysis. The MS/MS data generated from nanoLC/ESI-based IDA analysis were submitted to Mascot 2.2 for database searching using an in-house licensed Mascot local server and the search was performed to query the SwissProt database (taxonomy: Proteobacteria) with one missed cleavage site by semi-trypsin allowed. The peptide tolerance was set to 1.5 D and MS/MS tolerance was set to 0.6 D. Carbabamidomethyl modification of cysteine and oxidation of a methionine were set as variable modifications. Only significant scores for the peptides defined by Mascot probability analysis (www.matrixscience.com/help/scoring_help.html#PBM) greater than "identity" were considered for the peptide identification.

Construction of $ExoR_{c20}$-Expressing Plasmid

To construct a translational fusion of the exoR signal peptide and the ExoR C-terminal proteolytic product ($ExoR_{c20}$), the exoR signal peptide coding region along with the exoR promoter region and the $ExoR_{c20}$ (amino acids 81-268) coding region were obtained individually from two PCRs. The primers used to amplify the coding region for exoR promoter and ExoR signal peptide were exoRfHindIII-1 and $exoR_{90}w241r$, and those to amplify the coding region for $ExoR_{c20}$ were exoR90w241f and exoRrXhoI-2. After PCR and purification, the two fragments were ligated together via recombinant PCR using primers exoRfHindIII-1 and exoRrXhoI-2. This PCR product was then purified and digested with restriction enzymes HindIII and XhoI, and ligated with the vector pMB393 digested with the same enzymes to generate plasmid pHC567.

Construction of Plasmids Expressing ExoR Protein with Single-Amino Acid Mutations Single-amino acid mutations of ExoR were introduced via PCR site-directed mutagenesis. To construct pHC571 with the ExoR L81A mutation, two separate PCRs were run using primer pairs exoRfHindIII-1/exoRL81Ar and exoRL81Af/exoRrXhoI-2, and plasmid pHC510 DNA as template. Primers exoRL81Ar and exoRL81Af introduced a codon change resulting in an L-to-A mutation at position 81 of the ExoR protein. The two PCR DNA fragments were ligated together via recombinant PCR using primers exoRfHindIII-1 and exoRrXhoI-2. This PCR product was then purified and digested with restriction enzymes HindIII and XhoI, and ligated with vector pMB393 digested with the same enzymes to generate plasmid pHC567.

Using a similar approach, plasmid pHC572 was constructed with the W79A mutation created by primers exoRW79Ar and exoRW79Af, and pHC573 was constructed with the Y87A mutation created by primers exoRY87Ar and exoRY87Af.

Results

Extra Protein Bands in ExoR Profiles

Figure 4:
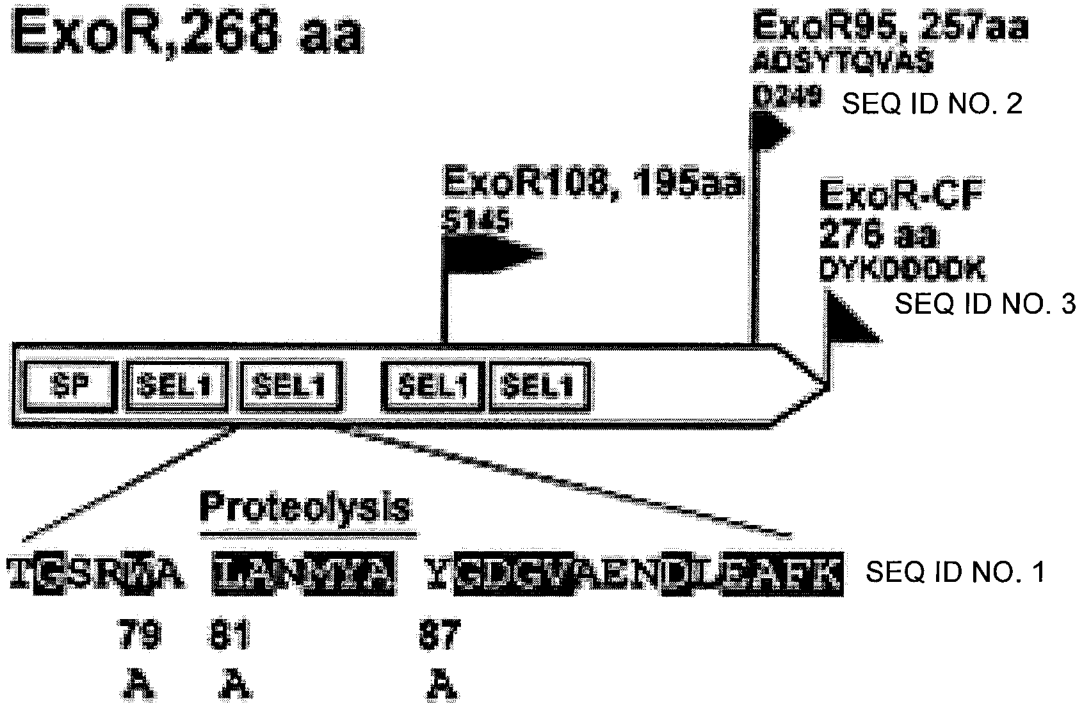
FIG. 4 is a schematic representation of the ExoR protein showing signal peptide (SP), four putative Sell protein-protein interaction domains (SEL1), a FLAG-tagged ExoR protein (ExoR-CF), two mutated ExoR proteins (ExoR95 and ExoR108), the proteolysis region of ExoR, the amino acids that are conserved (in black-shaded letters) around the proteolysis region, and the positions of the three amino acids that were mutated to alanine (A) for functional analyses.
Figure 5:
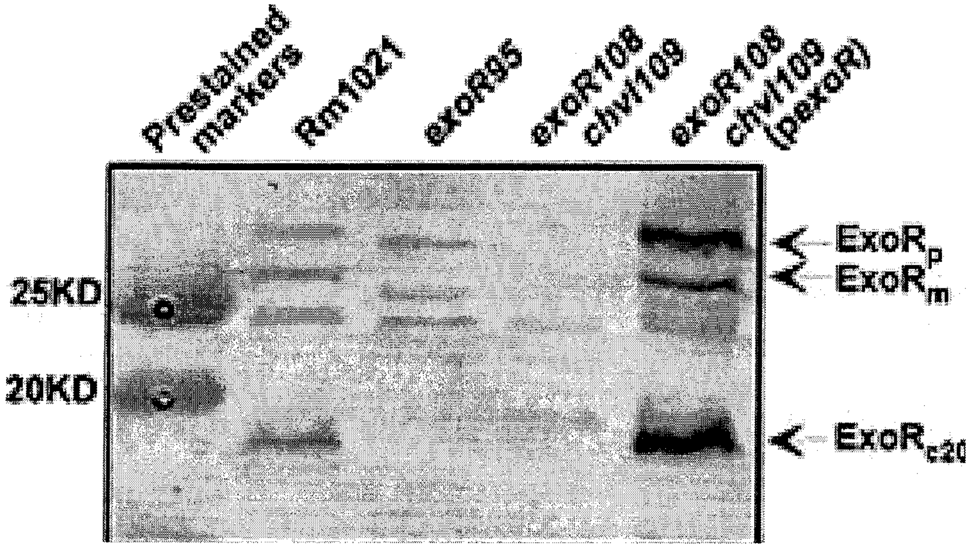
FIG. 5 is a Western blot showing ExoR protein profiles of the *S. meliloti* wild-type Rm1021, exoR95 mutant, exoR108chvI109 double mutant, and the double mutant exoR108chvI109 (pHC510), which is labeled as pexoR mutant expressing the wild-type exoR gene.

The ExoR protein autoregulates its own expression through the ExoS/ChvI system and it has been shown to exist in the 29-kD precursor form ($ExoR_p$) and the 26-kD active mature form ($ExoR_m$) without signal peptide (FIG. 4). The $ExoR_m$ form most likely interacts directly with the sensing domain of ExoS in the periplasm to regulate ExoS sensor activity. This would suggest that the amount of $ExoR_m$ is linked to the activity of ExoS and that this amount needs to be tightly regulated, perhaps by converting it into an inactive form. To find other possible forms of ExoR, ExoR polyclonal antibodies were prepared by using gel-purified N-terminal-labeled His-ExoR. When total cellular proteins from *S. meliloti* wild-type strain Rm1021 were resolved and probed with our ExoR polyclonal antibodies, three extra prominent protein bands of 20, 21, and 24 kD were detected, in addition to the known 29-kD $ExoR_p$ and 26-kD $ExoR_m$ (FIG. 5). To determine the origin of the 20-, 21- and 24-kD proteins, the ExoR profile of the wild-type strain was compared to that in the loss-of-function exoR95 mutant.

The exoR95 mutant is a transposon Tn5 insertion mutant; the site of the Tn5 insertion has been genetically mapped to the end of the exoR gene. To determine the size and amino acid sequence of the ExoR95 protein, the site of the transposon insertion was determined. Tn5 was found to be inserted between codons 248 and 249, replacing the original 20 C-terminal amino acids of ExoR with a new set of 9 amino acids in the ExoR95 protein. See provisional patent application 61/652,120. This suggested that if the ExoR95 protein is synthesized and exported to the periplasm like the wild-type ExoR, it should exist in 28-kD $ExoR95_p$ and 25-kD $ExoR95_m$ forms.

Western blot analysis showed that the exoR95 mutant not only has the predicted 28-kD $ExoR95_p$ and 25-kD $ExoR95_m$ forms (FIG. 5), but also the 21- and 24-kD proteins which were found in the wild type Rm1021 cells. It is also interesting that the 20-kD protein is missing from the exoR95 mutant. The 21- and 24-kD proteins are smaller than the 25-kD $ExoR95_m$, which makes it possible in theory for them to be derivatives of the 25-kD $ExoR95_m$ protein. Therefore, a strain with a smaller, or no ExoR protein was needed to help identify the origins of the 20-, 21-, and 24-kD proteins.

Construction of an exoR Mutant for Biochemical Analysis

Figure 6A:
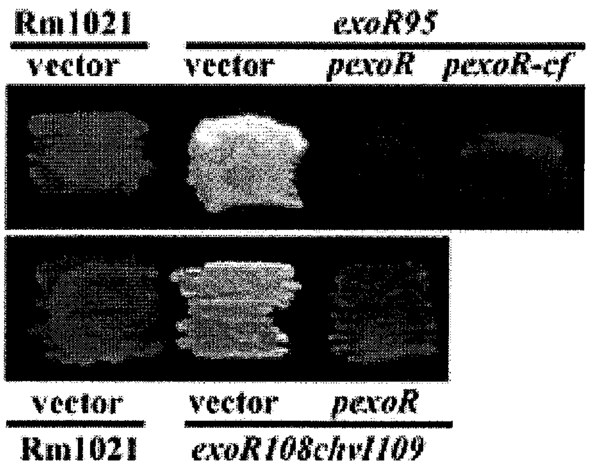
FIGS. 6A, 6B and 6C are a functional analyses of the wild-type ExoR protein and C-terminal FLAG-tagged ExoR proteins with each protein expressed in the exoR95 background and in the exoR108chvI109 double mutant background to determine its function in regulating succinoglycan production, as determined by the levels of colony brightness on calcofluor-containing medium (6A), and flagellum production as determined by the size of swimming colonies (6B) and the functions of these modified ExoR proteins in nodulation were measured according to the percentage of pink nodules (6C) in the exoR95 mutant background wherein the plasmids for the expression vector, pexoR and pexoR-cf are pMB393, pHC510, and pHC630, respectively.
Figure 6B:
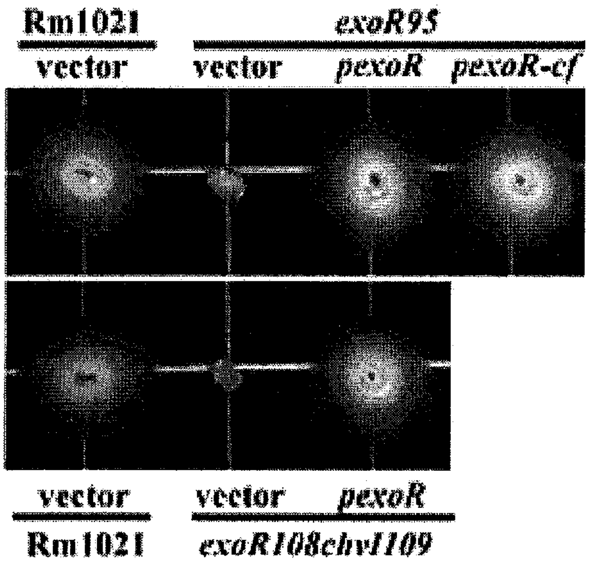

After multiple attempts, we were only able to obtain one exoR mutant—exoR108, resulting from the insertion of plasmid pHC508 carrying part of the exoR open reading frame (ORF). The ExoR108 protein is predicted to be a fusion of 144 N-terminal amino acids from ExoR and 51 C-terminal amino acids from the inserted suicide plasmid (FIG. 4). The exoR108 mutant overproduced succinoglycan and formed non-swimming colonies, similar to the exoR95 mutant. These exoR108 mutant phenotypes were complemented by the plasmid pHC510 expressing wild-type ExoR protein, suggesting that the exoR108 mutation is a loss-of-function mutation (FIG. 6A and FIG. 6B).

The difficulties in obtaining an exoR mutation, and prior findings of exoR suppressor mutations in the exoS and chvI genes, prompted us to check exoS and chvI in the exoR108 mutant. Interestingly, while there was no mutation in the exoS gene, there was a single G to A nucleotide change at position 325 in the chvI gene in the exoR108 mutant. This mutation results in a change in amino acid 109 of the ChvI protein from V to M, so the exoR108 mutant is in fact an exoR108chvI109 double mutant. It was possible to transduce the exoR108 mutation from the exoR108chvI109 mutant into wild-type Rm1021 expressing the wild-type exoR gene from plasmid pHC510, but not into Rm1021 itself. This raised the possibility that the exoR gene can only be interrupted to generate the exoR108 mutation in the presence of either a plasmid-borne copy of the exoR gene or the chvI109 mutation. These findings suggest that it would not be possible to rule out the possibility that the chvI109 mutation could contribute to the phenotype of the exoR108chvI109 double mutant, and the mutant could therefore only be used for biochemical analyses of ExoR proteins in this study.

A Novel 20-kD Form of the ExoR Protein

Figure 7A:
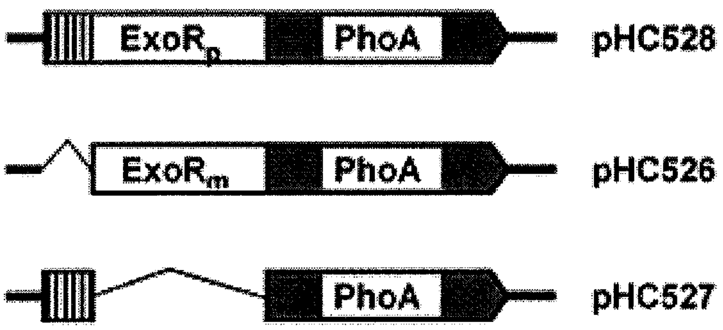
FIGS. 7A, 7B and 7C show the cellular location of ExoR protein and site of proteolysis. Schematic representation of three different ExoR-PhoA fusions (7A) and their corresponding phosphatase activities in the *S. meliloti* Rm8002 background (7B). Boxes with vertical stripes represent ExoR signal peptide. ExoR protein profiles were determined by western blot (7C) for wild-type ExoR protein expressed from pHC518 (pR) and the ExoR protein without signal peptide, $ExoR_m$, expressed from plasmid pHC641($pR_m$) in the exoR95 mutant background.
Figure 7B:
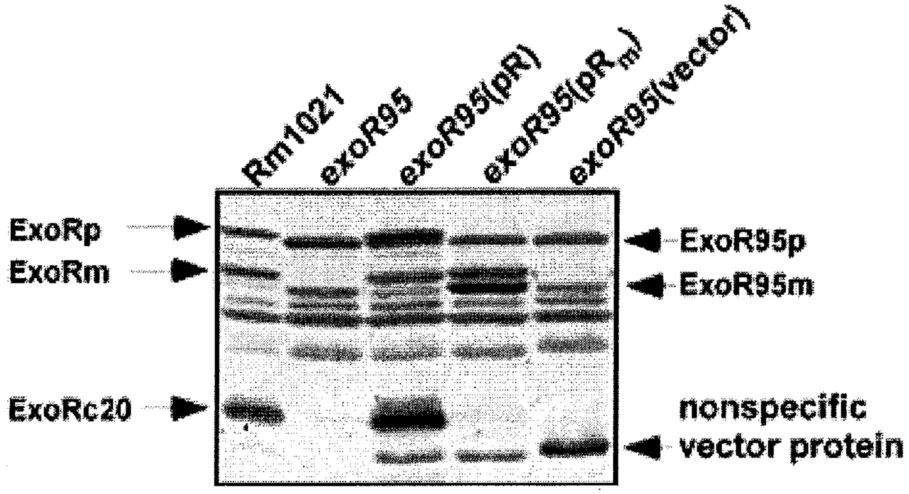

Three proteins at 29, 26, and 20 kD stood out clearly in the ExoR protein profiles of the exoR108chvI109 double mutant with plasmid pHC510 expressing wild-type ExoR protein while the intensity of 21- and 24-kD bands remained the same as the exoR108chvI109 double mutant without plasmid pHC510 (FIG. 5). The positions of 29, 26, and 20 kD proteins matched those of the three protein bands in wild-type strain Rm1021 (FIG. 5). Since the 21- and 24-kD proteins were present in wild-type Rm1021 as well as in the exoR95 and exoR108 mutants, they are most likely nonspecific proteins. Together, these findings suggest that the ExoR protein exists in three different forms, 29, 26, and 20 kD. The finding of the previously unknown 20-kD ExoR protein suggests that ExoR could be the target of proteolysis. $ExoR_m$ is digested in the periplasm The 20-kD ExoR protein, designated $ExoR_{c20}$, could be the proteolysis product of either $ExoR_p$ in the cytoplasm or $ExoR_m$ in the periplasm. To find a way to restrict ExoR in either the cytoplasm or periplasm, the role of its signal peptide was further examined. The entire ExoR protein ($ExoR_p$), ExoR without the signal peptide ($ExoR_m$), and the ExoR signal peptide were separately fused to PhoA (FIG. 7A). The presence of the signal peptide was sufficient for ExoR-PhoA fusion and PhoA to be exported to the periplasm, where it displayed phosphatase activity as indicated by the blue color of the colonies on medium containing XP (5-bromo-4-chloro3-indolyl phosphate) (FIG. 7B). In the absence of signal peptide, the $ExoR_m$-PhoA fusion protein remained inside the cells as indicated by the white color of the colonies (FIG. 7B).

Figure 7C:
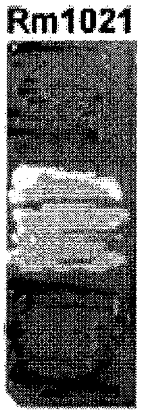

To help determine the site of $ExoR_m$ proteolysis, wild-type ExoR and $ExoR_m$ were expressed in the exoR95 mutant from plasmids pHC518 and pHC641 to deliver $ExoR_m$ to the periplasm or cytoplasm, respectively. When wild-type ExoR was expressed in the exoR95 mutant from plasmid pHC518, all three forms of the wild-type ExoR: $ExoR_p$, $ExoR_m$, and $ExoR_{c20}$, were clearly visible, in addition to $ExoR95_p$ and $ExoR95_m$ (FIG. 7C). In contrast, when $ExoR_m$ was expressed in the exoR95 mutant from plasmid pHC641, the $ExoR_m$ protein as well as $ExoR95_p$ and $ExoR95_n$, were found, but very little $ExoR_{c20}$ protein was detected. This suggests that $ExoR_m$ is very ineffectively processed inside the cytoplasm. Taken together, these findings suggest that $ExoR_m$ is digested efficiently in the periplasm to yield the 20-kD form. This conclusion was further confirmed by direct isolation and sequencing of the ExoR proteolysis product from the periplasm, as described below.

Functional Analyses of C-Terminal FLAG-Tagged ExoR Protein

Figure 6C:
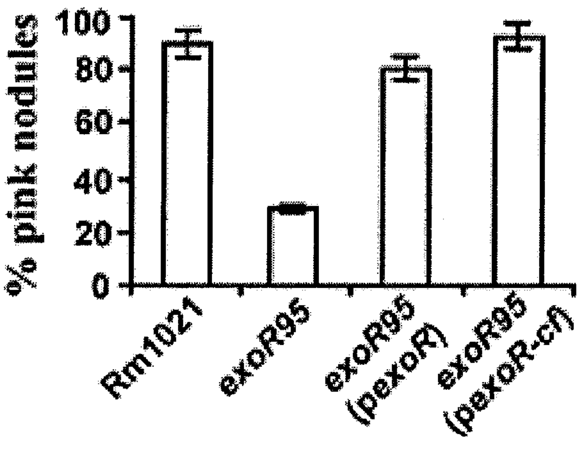

To determine whether the 20 kD form of ExoR shares the same C-terminus with $ExoR_m$, ExoR-CF, an ExoR with an 8-amino acid C-terminal-FLAG tagged ExoR (see provisional patent application 61/652,120), was generated by fusing the FLAG tag to the ExoR C terminus (FIG. 4). ExoR-CF was expressed from plasmid pHC630 with the native exoR promoter. Our results showed that ExoR-CF was as effective at complement the succinoglycan-overproduction phenotype of the exoR95 mutant as the wild-type ExoR protein expressed from plasmid pHC510 (FIG. 6A). Similarly, ExoR-CF was as effective as the wild-type ExoR in restoring swimming activity (FIG. 6B) and nodulation of alfalfa plants of the exoR95 mutant, as determined by the percentage of pink nodules (FIG. 6C). These findings suggest that the biochemical analysis of ExoR-CF should reflect the properties of the wild-type ExoR protein.

The C Terminus of the 20-kD Form of ExoR

Figures 8A, 8B:
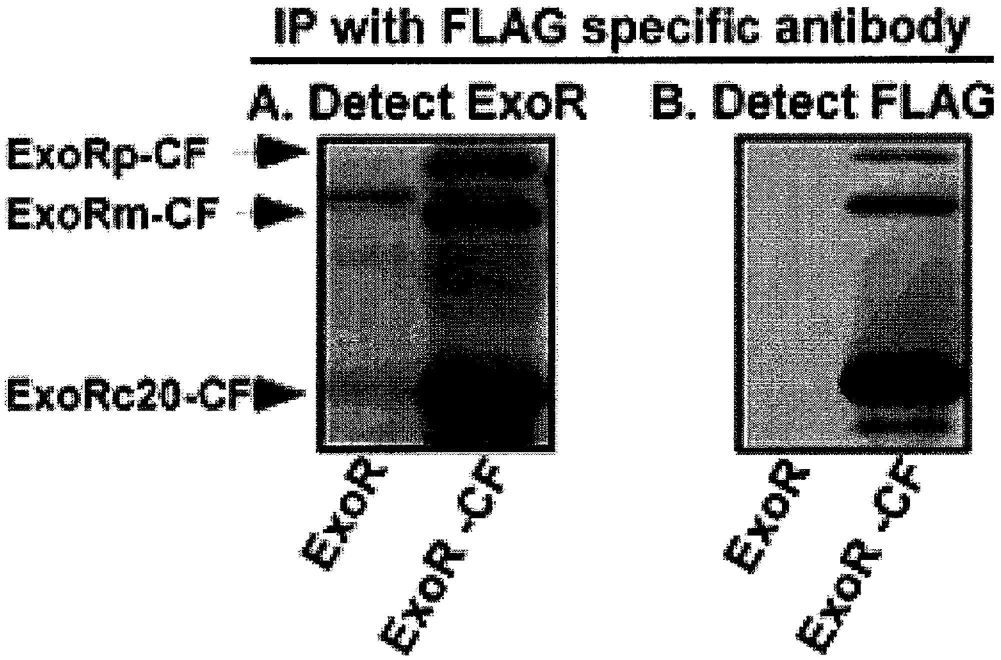
FIGS. 8A and 8B are Western blot protein profiles of the exoR95 mutant carrying plasmid pHC510 and pHC630 expressing wild-type ExoR and ExoR-CF, respectively. Proteins were immunoprecipitated (IP) with FLAG antibody, and detected with either ExoR polyclonal antibodies (8A) or FLAG antibody (8B)

The C terminus of the 20 kD form of ExoR could be determined by identifying which form of ExoR protein retains the FLAG tag. Total proteins from the exoR95 mutant expressing ExoR and ExoR-CF proteins from plasmids pHC510 and pHC630, respectively, were prepared, immunoprecipitated with FLAG-specific monoclonal antibody, and probed with either our ExoR polyclonal antibodies (FIG. 8A) or the FLAG-specific monoclonal antibody (FIG. 8B). Wild-type ExoR protein without a FLAG tag could not be precipitated with the FLAG-specific antibody so it was not detected by either antibody. Our analysis of C-terminal FLAG-tagged ExoR-CF showed that all three different forms of ExoR were detected by both ExoR and FLAG antibodies (FIGS. 8A and 8B). This suggests that $ExoR_p$, $ExoR_m$ and $ExoR_{c20}$ were all carrying the FLAG tag. Altogether, these findings suggest that the 20-kD form of ExoR derives from the C-terminal side of the ExoR protein (hence its designation as $ExoR_{c20}$).

The N Terminus of the 20-kD ExoR Fragment and the Site of ExoR Proteolysis

To identify the N-terminal amino acid of $ExoR_{c20}$, which is also the site of ExoR proteolysis, the C-terminal FLAG-tagged ExoR-CF proteins were isolated directly from the periplasm of *S. meliloti* cells using osmotic shock and immunoprecipitation with commercial monoclonal FLAG-tag antibody. $ExoR_{c20}$-CF, $ExoR_{c20}$ with C-terminal FLAG tag, was first isolated directly from a crude preparation of periplasmic proteins by immunoprecipitation, then resolved by SDS-PAGE, transferred to a (PVDF) membrane, and stained with Coomassie blue. A piece of membrane containing $ExoR_{c20}$-CF was used to identify its N-terminal amino acid by peptide mapping.

The results of the peptide mapping showed that the N-terminal amino acid of $ExoR_{c20}$—CF is L, and that it is amino acid 81 in the ExoR protein. The confidence in this finding was measured with Mascot probability analysis (www.matrixscience.com/help/scoring_help.html#PBM). A Mascot value of 59 represents 99% confidence. The Mascot value for L as the N-terminal amino acid was 94, indicating more than 99% confidence in the identification. Interestingly, amino acids 84, 85, 86 and 87 were also identified as N-terminal amino acids with Mascot value, ranging between values of 85 and 111. This suggested that ExoR proteolysis could take place between amino acids 80 and 87 of the ExoR protein to yield a mixture of 181 to 188 amino acid long peptides (FIG. 4). These peptides could be the result of a single digestion between amino acid 80 and 81 followed by additional digestion, or they could be the result of a single random digestion within the region of amino acid 80 to 87. The preparation method for peptide mapping used here precluded us from determining which fragment was the dominant form. Taken together, these findings suggest the strong likelihood of $ExoR_m$ protein being further digested between amino acids 80 and 87 to yield $ExoR_{c20}$ a set of 181 to 188 amino acid (19.9 to 20.6-kD) peptides.

A large number of ExoR orthologs have been discovered through genome sequencing, although few of them have been characterized in detail. Sixteen ExoR orthologs were aligned based on their overall amino acid identity, ranging from 97% to 51% (FIG. 9). Despite the dramatic decrease in the overall amino acid identity, however, the amino acid sequence around the ExoR proteolysis sites remains highly conserved among the ExoR orthologs (FIG. 9). This raises the possibility that ExoR proteolysis is conserved among other ExoR orthologs, and that proteolysis could be a common molecular signaling mechanism for ExoR proteins in different bacteria.

$ExoR_{c20}$ does not Function in the ExoS/ChvI System

The discovery that both $ExoR_m$ and $ExoR_{c20}$ are stably maintained in the wild-type Rm1021 cells, and that $ExoR_{c20}$ is absent in the loss-of-function exoR95 mutant, raised the possibility that $ExoR_{c20}$ is the functional form of the protein. To examine the function of $ExoR_{c20}$ directly, the longest form of $ExoR_{c20}$ with 188 amino acids was fused to the 30-amino-acid ExoR signal peptide to generate SP-$ExoR_{ao}$ expressed from pHC567. When total proteins from the exoR108chvI109 mutant expressing SP-$ExoR_{c20}$ were probed with ExoR polyclonal antibodies, both SP-$ExoR_{c20}$ and $ExoR_{c20}$ were detected (FIG. 10A). This suggests that SP-$ExoR_{c20}$ is expressed, processed, and stably maintained without its signal peptide in the periplasm.

To test the function of $ExoR_{c20}$, the SP-$ExoR_{c20}$ protein was expressed in the wild-type strain Rm1021 and the exoR95 mutant. The presence of the SP-$ExoR_{c20}$-expressing plasmid pHC567 did not change either succinoglycan or swimming phenotypes for either wild-type Rm1021 or the exoR95 mutant (FIGS. 10C and 10D). These results, along with the finding that the wild-type ExoR protein was able to complement the phenotypes of the exoR95 mutant (FIG. 5), suggest that the ExoR proteolysis product, $ExoR_{c20}$, does not function in regulating the production of succinoglycan or flagella.

ExoR Proteolysis and Regulatory Functions are Altered by Point Mutations

Our finding of functional $ExoR_m$ and nonfunctional $ExoR_{e20}$ co-existing in the periplasm raised the possibility that the amount of $ExoR_m$ is maintained at a certain level and that any changes to the level of $ExoR_m$ will alter the function of the ExoR protein. To test this possibility, two highly conserved amino acids at positions 79 and 81, and one nonconserved amino acid at position 87 were changed individually to A (alanine) (FIG. 4). When these three mutant ExoR proteins, ExoRW79A, ExoRL81A, and ExoRY87A, were expressed from plasmids pHC571, pHC572, and pHC573, respectively, in the exoR108chvI109 double mutant, the level of the $ExoR_m$ form was significantly reduced for the ExoRL81A mutant, slightly reduced for the ExoRW79A mutant, but not changed for the ExoRY87A mutant (FIG. 11A). These suggest that the L81A mutation may have reduced the amount of $ExoR_m$ form of ExoR mutant protein in the cells.

The regulatory functions of the three mutated ExoR proteins were examined by assessing their abilities to complement the succinoglycan-producing (represented by calcofluor brightness) and non-swimming phenotypes of the exoR95 mutant (FIGS. 11C, 11D). Compared to the wild type ExoR protein, the ExoRL81A protein was not able to complement neither succinoglycan producing nor non-swimming phenotypes of the exoR95 mutant, and it is therefore a loss-of-function mutation. Both ExoRW79A and ExoRY87A proteins partially complemented both succinoglycan producing and non-swimming phenotypes of the exoR95 mutant. The ExoRY87A was more effective than ExoRW79A in complementing the succinoglycan producing phenotype. These results suggest that both ExoRW79A and ExoRY87A are functional and that ExoRY87A is more effective than ExoRW79A but less effective than wild type ExoR.

The combined biochemical and functional analyses of the three mutant ExoR proteins suggest that the level of $ExoR_m$ is linked to the regulatory function of ExoR protein. This raises the possibility that ExoR proteolysis can be modulated by environmental or plant signals to regulate the production of succinoglycan, flagella, and many other cellular products required for symbiosis.

Discussion

Recent publications have shown that *S. meliloti* ExoR protein most likely functions as the repressor of the ExoS sensor, as part of the ExoR autoregulation pathway, which allows it to indirectly regulate the expression of a large number of genes required for host invasion and symbiosis. Both genetic and biochemical data appear to support the model that ExoR interacts with ExoS periplasmic sensing domain directly to suppress ExoS, keeping it in an off state. It follows that ExoR suppression of ExoS would have to be relieved during nodulation so that the expression of the invasion and symbiosis genes could be turned on to support the nodulation. However, the molecular mechanism mediating the release of ExoR suppression of ExoS is not clear.

One simple and attractive model for the relief of ExoR suppression is a reduction in the amount of ExoR protein in its mature and active form, $ExoR_m$, by changing it to an inactive form through proteolysis or modification. To monitor such changes in $ExoR_m$ on a western blot, antibodies are required that can recognize the entire ExoR protein and a *S. meliloti* strain to provide the genetic background with no ExoR protein. While generating ExoR-specific polyclonal antibodies was relatively straightforward, engineering a *S. meliloti* strain with no ExoR proved to be challenging.

Two complementary approaches were followed to find a clean background for the analysis of ExoR protein. The first was to determine the status of ExoR in the original loss-of-function exoR95 mutant. Our analysis showed that the mutated ExoR95 protein can be easily found in two forms $ExoR95_p$ and $ExoR95_m$. This makes it more difficult to monitor the changes in wild-type ExoR protein since these two forms are just slightly smaller than the wild type, as predicted based on the site of the exoR95 mutation. The second approach, which was to generate an ExoR-deletion mutation, turned out to be much more difficult. The only new exoR mutation generated from this effort was the exoR108chvI109 double mutant with a plasmid insertion in the exoR gene. The exoR108 mutation can be transduced from the exoR108chvI109 double mutant into wild-type strain Rm1021 (pHC510) expressing exoR gene from plasmid pHC510, but not into Rm1021 alone. This suggests that the presence of a chvI109 mutation is likely to be essential for the existence of the exoR108 mutation in the *S. meliloti* genome. This led us to decide that even though the succinoglycan- and flagellum-production phenotypes of the exoR108 mutant can be complemented by the wild-type exoR gene, the exoR108chvI109 mutant would only be used for biochemical analysis of the ExoR protein in this study.

Our comparative analysis of the ExoR protein profiles in a different genetic background led to the discovery of a new form of ExoR protein, $ExoR_{c20}$, while confirming the existence of the $ExoR_p$ and $ExoR_m$ forms. Two lines of evidence suggest that $ExoR_{c20}$ is the periplasmic proteolysis product of $ExoR_m$. The first is that when $ExoR_{c20}$ was sequestered inside the cytoplasm by removing its signal peptide, no $ExoR_{c20}$ was detected. The second is the direct isolation of $ExoR_{c20}$ from the periplasm. While $ExoR_{c20}$ has a single C terminus, which is the same as that of wild-type ExoR, it appears to have multiple N termini. When a gel-purified single $ExoR_{c20}$ protein band was used for N-terminus mapping, the results demonstrated N termini at positions 81, 84, 85, 86 and 87 of the ExoR ORF. These fragments may be produced by one or multiple enzymes in parallel, or produced by one specific endoprotease digestion followed by multiple exoprotease digestions. While further analysis of these proteolysis products is important to identify the protease involved in $ExoR_m$ proteolysis, the more important finding of this study is the fact that $ExoR_m$ is the subject of proteolysis. This could serve as the molecular mechanism that reduces the active $ExoR_m$, and releases suppression of the ExoS sensor.

The presence of stably maintained $ExoR_{c20}$ in wild-type Rm1021 but not in the loss-of-function exoR95 mutant raised the question of whether $ExoR_{c20}$ functions in the ExoR-ExoS/ChvI signal-transduction pathway. To address this question, the longest form of $ExoR_{c20}$ was fused directly to the ExoR signal peptide and expressed in the wild-type Rm1021 and the exoR95 mutant. The presence of $ExoR_{c20}$ in both strains was confirmed by western blot. The presence of $ExoR_{c20}$ did not alter the succinoglycan and swimming phenotypes of either the wild type or the exoR95 mutant. This suggests that $ExoR_{c20}$ does not play any significant role in regulating succinoglycan or flagellum production. More importantly, it also suggests that digesting $ExoR_m$ to $ExoR_{c20}$ might function as a molecular mechanism regulating the amount of $ExoR_m$ in the periplasm.

For proteolysis of $ExOR_m$ to serve as a mechanism regulating the function of ExoR, modulation of the amount of $ExoR_m$ should change the regulatory function of ExoR. To test this hypothesis, the highly conserved amino acid leucine (L) at the site of the proteolysis was changed to alanine (A), generating ExoRL81A. In addition, similar site-directed mutations were generated for another conserved amino acid, giving ExoRW79A, and a nonconserved amino acid, giving ExoRY87A. The mutation of the nonconserved amino acid 87 showed no detectable change in the levels of $ExoR_m$ protein or the regulatory function of ExoR. Compared to the wild type ExoR, the ExoRW79A mutation of the conserved W (tryptophan) slightly decreased $ExoR_m$ level and slightly reduced the regulatory function of ExoR. The ExoRL81A mutation, which changes the proteolysis site (amino acids 80-81), dramatically decreased the amount of $ExoR_m$ protein and completely abolished the regulatory function of the ExoR protein. Altogether, these findings link reduction of $ExoR_m$ and the regulatory function of the ExoR protein. In addition, our finding of single amino acid change, the L81A mutation, enhancing $ExoR_m$ proteolysis raises the possibility that the ExoR proteolysis sequence is fine-turned for optimum control of proteolysis instead of efficient proteolysis. The better control of $ExoR_m$ proteolysis will allow *S. meliloti* cells to sense and react more effectively to the presence of yet to identified host or environmental signals.

Figure 12:
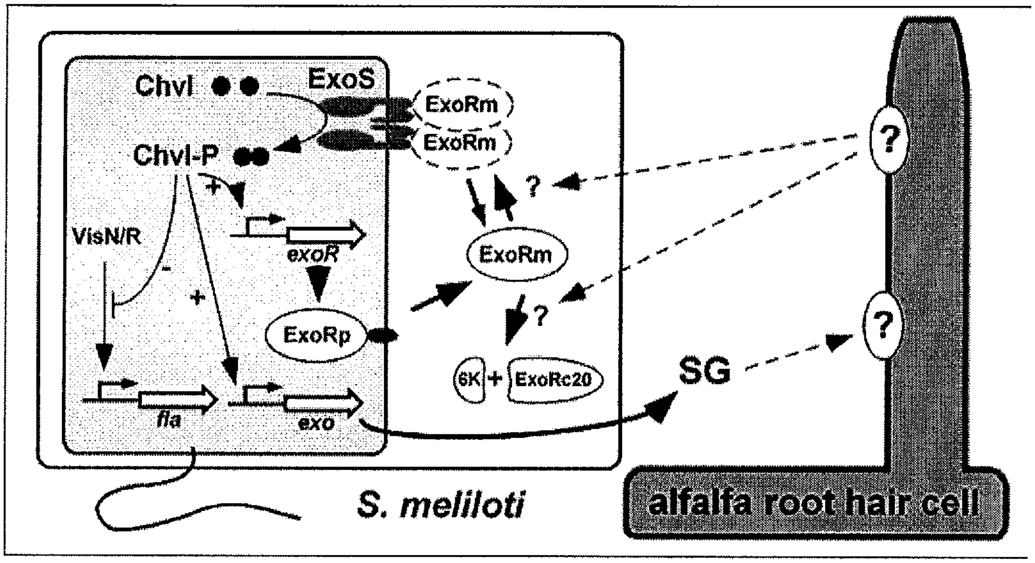
FIG. 12 is a model of the ExoR-ExoS/ChvI signal-transduction pathway. It is hypothesized that the active mature form of ExoR, $ExoR_m$, is digested via slow proteolysis in wild-type cells. An increase in ExoR proteolysis triggered by environmental or plant signals or mutations in the exoR genes will reduce the amount of $ExoR_m$ binding to the ExoS sensing domain, leading to the activation of ExoS sensor and the activation or suppression of expression of the genes regulated by the ExoS/ChvI two-component regulatory system.

A model is proposed to integrate the new findings from this study with those from previous work (FIG. 12). We propose that the newly synthesized precursor form of ExoR, $ExoR_p$, is directed to the membrane and secreted into the periplasm without its signal peptide, to form the mature $ExoR_m$. The amount of periplasmic $ExoR_m$ in free-living *S. meliloti* cells is kept in equilibrium by both interaction with ExoS and its steady proteolysis, forming $ExoR_{c20}$. This model is supported by previous results (5, 33, 53, 55) and our finding that the point mutation L81A reduces the level of $ExoR_m$ and disables the regulatory function of the ExoRL81A protein. The ExoR95 mutant protein might have an altered conformation such that it is resistant to proteolysis and thus no proteolytic product, $ExoR95_{c19}$, equivalent of $ExoR_{20}$, is detectable, or that the resulting $ExoR95_{c19}$ is not stable.

Our model would predict that plant or environmental signals would alter the rate of $ExoR_m$ proteolysis, thereby changing the level of ExoR suppression of ExoS. This would allow *S. meliloti* cells to modulate the production of succinoglycan and flagella, as well as the expression of many other ExoR-ExoS/ChvI pathway-regulated genes, to support the establishment of symbiosis in response to the presence of plant host or environmental signals. Based on this prediction, we are currently screening for conditions that can change the level of succinoglycan production by the wild type Rm1021.

Close homologs of ExoR, as well as of ExoS and ChvI of the ExoR-ExoS/ChvI signal-transduction pathway have been found in the genomes of more than 40 different bacterial species. The regulatory mechanisms and the genes regulated by these systems are, with a few exceptions, unknown. When ExoR homologs are aligned in order of decreasing overall homology from 93% to 50% to the *S. meliloti* ExoR protein, the levels of homology around the region of proteolysis remain unchanged. The high levels of conservation of protein sequence around the $ExoR_m$ proteolysis region raises the possibility that ExoR proteolysis is a common molecular mechanism mediating bacterial sensing in the presence of their hosts or of changes in their environment.

Bacterial periplasmic proteases have been shown to participate in bacterial sensing of environmental signals in several systems. An *Escherichia coli* membrane-bound protease, DegS, which is activated by unassembled outer-membrane porins, cleaves the periplasmic domain of the membrane-anchored regulator, RseA. This triggers further cleavage of RseA by a metalloprotease, YaeL, to release $\sigma^E$, which normally attaches to RseA. The free $\sigma^E$ turns on the expression of stress-related genes. In the case of a polarity determinant of Caulobacter, PodJ, the periplasmic domain of PodJ is also regulated through cleavage into small fragments by a periplasmic protease, PerP. The example that is closest to *S. meliloti* ExoR is the function and regulation of the *E. coli* periplasmic adaptor protein, CpxP, which is involved in sensing pH variations to regulate membrane lipid composition. The CpxP protein interacts with and inhibits the periplasmic sensing domain of the CpxA protein, the sensor of the CpxA/CpxR two-component system. The periplasmic serine protease, DegP, is activated by general envelope disruptions, including pH changes, and cleaves the CpxP protein, thereby removing CpxP from the CpxA sensor. This results in the activation of CpxA sensor and the expression of its regulated genes. Our finding that ExoR is the subject of proteolysis in the periplasm suggests a regulatory role similar to that of RseA, PodJ and CpxP.

While it has been well documented that ExoR, ExoS, and ChvI play essential roles in symbiosis, it is not known what environmental signals are transmitted through the ExoR-ExoS/ChvI signal-transduction pathway. The factors that might function upstream of ExoR are also unknown. Our finding of ExoR proteolysis in the periplasm suggests a protease(s) as a key factor upstream of ExoR. The proteolysis of ExoR might be regulated by other proteins in the periplasm through protein-protein interactions or by other enzymes that modify ExoR. These possibilities will be further investigated to gain more insight into the regulation of ExoR and the function of the ExoR-ExoS/ChvI signal-transduction pathway. The results of our analysis of ExoR will no doubt be helpful in understanding and combating the pathogenicities of *A. tumefaciens* and *B. abortus*, as well as many other host-interacting bacteria that rely on homologs of the ExoR-ExoS/ChvI signal-transduction pathway.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for modulating a bacterial invasion switch by changing the proteolysis of ExoR protein, the method comprising:

administering a protease inhibitor to a bacterium such that proteolysis of the mature form of $ExoR_m$ is prevented, thereby keeping the bacterium in a non-pathogenic state;

quantifying a first $ExoR_m$ level after the step of administering wherein the first $ExoR_m$ level is lower than a second $ExoR_m$ level prior to the step of administering, wherein the protease inhibitor is phenylmethanesulfonylfluoride or phenylmethylsulfonyl fluoride (PMSF).

2. The method as recited in claim 1, further comprising introducing the bacterium to an animal.

3. The method as recited in claim 1, further comprising introducing the bacterium to a plant.

4. The method as recited in claim 1, wherein the step of determining comprises testing the bacterium to verify the bacterium is in the non-pathogenic state.

5. A method for modulating a bacterial invasion switch by changing the proteolysis of $ExoR_m$ protein, the method comprising:

exposing a bacterium to a cell penetration agent;

administering a protease inhibitor to a periplasm of the bacterium such that proteolysis of the mature form of $ExoR_m$ is prevented, thereby keeping the bacterium in a non-pathogenic state, wherein the cell penetration agent facilitates the step of administering the protease inhibitor to the periplasm;

quantifying a first $ExoR_m$ level after the step of administering wherein the first $ExoR_m$ level is lower than a second $ExoR_m$ level prior to the step of administering, wherein the protease inhibitor is phenylmethanesulfonylfluoride or phenylmethylsulfonyl fluoride (PMSF).

6. The method as recited in claim 5, wherein the cell penetration agent is a detergent.

7. The method as recited in claim 6, wherein the detergent is sodium dodecyl sulfate (SDS).

8. The method as recited in claim 5, wherein the cell penetration agent is a cell-penetrating peptide.

9. The method as recited in claim 5, further comprising introducing the bacterium to an animal.

10. The method as recited in claim 5, further comprising introducing the bacterium to a plant.

11. The method as recited in claim 5, further comprising testing the bacterium to verify the bacterium is in the non-pathogenic state.

* * * * *